United States Patent
Weksler et al.

(10) Patent No.: US 12,306,172 B2
(45) Date of Patent: May 20, 2025

(54) METHOD AND SYSTEM FOR ANALYZING PROSTATE BIOPSY

(71) Applicant: ProSight Ltd., Bat Yam (IL)

(72) Inventors: Meir Weksler, Bat Yam (IL); Avi Simon, Tel-Aviv (IL)

(73) Assignee: ProSight Ltd., Bat Yam (IL)

( * ) Notice: Subject to any disclaimer, the term of this patent is extended or adjusted under 35 U.S.C. 154(b) by 343 days.

(21) Appl. No.: 17/627,672

(22) PCT Filed: Jul. 16, 2020

(86) PCT No.: PCT/IL2020/050800
§ 371 (c)(1),
(2) Date: Jan. 16, 2022

(87) PCT Pub. No.: WO2021/009762
PCT Pub. Date: Jan. 21, 2021

(65) Prior Publication Data
US 2022/0260507 A1 Aug. 18, 2022

Related U.S. Application Data

(60) Provisional application No. 62/875,140, filed on Jul. 17, 2019.

(51) Int. Cl.
*G01N 33/483* (2006.01)
*G01N 23/223* (2006.01)
*G16H 50/20* (2018.01)
*G16H 70/60* (2018.01)

(52) U.S. Cl.
CPC ....... *G01N 33/4833* (2013.01); *G01N 23/223* (2013.01); *G16H 50/20* (2018.01); *G16H 70/60* (2018.01); *G01N 2223/076* (2013.01); *G01N 2223/402* (2013.01); *G01N 2223/6126* (2013.01)

(58) Field of Classification Search
CPC .. G01N 33/4833; G01N 23/223; G16H 70/60; G16H 50/20
See application file for complete search history.

(56) References Cited

U.S. PATENT DOCUMENTS

| | | |
|---|---|---|
| 9,052,319 B2 | 1/2015 | Simon et al. |
| 2002/0119463 A1 | 8/2002 | Faris et al. |
| 2007/0292900 A1 | 12/2007 | Frederickson et al. |
| 2009/0170075 A1 | 7/2009 | Petrovis et al. |
| 2011/0046204 A1 | 2/2011 | Costello et al. |
| 2015/0097868 A1 | 4/2015 | Banerjee et al. |
| 2016/0222461 A1 | 8/2016 | Wilson et al. |

FOREIGN PATENT DOCUMENTS

WO WO 2021/009762 1/2021

OTHER PUBLICATIONS

International Preliminary Report on Patentability Dated Jan. 27, 2022 From the International Bureau of WIPO Re. Application No. PCT/IL2020/050800. (8 Pages).
International Search Report and the Written Opinion Dated Oct. 23, 2020 From the International Searching Authority Re. Application No. PCT/IL2020/050800. (10 Pages).
Cortesi et al. "Clinical Assessment of the Cancer Diagnostic Value of Prostatic Zinc: A Comprehensive Needle-Biopsy Study", The Prostate, 68(9): 994-1006, Published Online Apr. 2, 2008.
Cortesi et al. "Evaluating the Cancer Detection and Grading Potential of Prostatic-Zinc Imaging: A Simulation Study", Physics in Medicine and Biology, 54(3): 781-796, Published Online Jan. 9, 2009.
Costello et al. "The Clinical Relevance of the Metabolism of Prostate Cancer; Zinc and Tumor Suppression: Connecting the Dots", Molecular Cancer, 5(17): 1-13, Published Online May 15, 2006.
Costello et al. "Zinc and Prostate Cancer: A Critical Scientific, Medical, and Public Interest Issue (United States)", Cancer Causes and Control, 16(8): 901-915, Oct. 2005.

*Primary Examiner* — Jerry Lin

(57) ABSTRACT

A method of analyzing a biopsy sample containing tissue extracted from a prostate gland of a subject comprises measuring zinc level and an epithelial glandular tissue concentration in the sample, determining the likelihood that the sample is cancerous based on at least the zinc level and the epithelial glandular tissue concentration in the sample, and generating an output indicative of the likelihood.

16 Claims, 12 Drawing Sheets

METHOD AND SYSTEM FOR ANALYZING PROSTATE BIOPSY

RELATED APPLICATIONS

This application is a National Phase of PCT Patent Application No. PCT/IL2020/050800 having International filing date of Jul. 16, 2020, which claims the benefit of priority under 35 USC § 119(e) of U.S. Provisional Patent Application No. 62/875,140 filed on Jul. 17, 2019. The contents of the above applications are all incorporated by reference as if fully set forth herein in their entirety.

FIELD AND BACKGROUND OF THE INVENTION

The present invention, in some embodiments thereof, relates to tissue analysis and, more particularly, but not exclusively, to a method and system for analyzing prostate biopsy.

The correlation between local zinc (Zn) content and Prostate Cancer (PCa) is known. For example, a series of papers by Cortesi relates to an extensive clinical study [see, e.g., Cortesi, M. et al., 2009; Physics in Medicine and Biology, 54(3), 781-796. Cortesi, M. et al., 2008; The Prostate, 68(9), 994-1006.], and a series of papers by Costello and Franklin describe the metabolism of Zn and PCa [see, e.g., Costello, L. C. & Franklin, R. B., 2006; Molecular Cancer, 5, 17. Costello, L. C. et al., 2005; Cancer Causes & Control: CCC, 16(8), 901-915]

PCa biopsy is currently performed with the use of ultrasound (US) for organ definition and localization by the urologist in either Trans Rectal (TRUS) or Trans Perineal (TP) biopsy. TRUS biopsy is performed according to clinical practice schemes, incorporating the removal of biopsy cores, typically from the lateral and mid-lateral posterior side of the prostate. Current standard is about 12 cores but in many medical centers 14-16 core procedures are executed per biopsy. TP biopsy uses a template and typically involves the removal of more than 24 cores (saturated biopsy).

Known in the art is a biopsy guidance technique that combines magnetic resonance imaging (MRI) and TRUS, and referred to as MRI-TRUS Fusion guided biopsy. In this technique, the prostate is scanned by MRI and suspected sites are identified in the scan. TRUS images are then fused with the MRI scan, and the needles are then guided for removal of cores from the identified suspected sites. The results of the TRUS biopsy are typically provided to the physician or patient one or more weeks following the procedure.

Use of the depletion of Zn content in a biopsy location for guidance of prostate biopsy was described in U.S. Pat. No. 9,052,319 to Simon et al. In this technique, the guidance information is derived from differences in the Zn levels measured on fresh biopsy cores coming from adjacent sites in the prostate. Simon et al discloses the use of an X-Ray Fluorescence (XRF) device for determining the concentration level of Zn (hereinafter "Zn") along a given biopsy core.

SUMMARY OF THE INVENTION

According to an aspect of some embodiments of the present invention there is provided a method of analyzing a biopsy sample containing tissue extracted from a prostate gland of a subject. The method comprises: measuring zinc level and an epithelial glandular tissue concentration in the sample; determining the likelihood that the sample is cancerous based on at least the zinc level and the epithelial glandular tissue concentration in the sample; and generating an output indicative of the likelihood.

According to some embodiments of the invention the method comprises calculating a ratio between the zinc level and the epithelial glandular tissue concentration, wherein the determining the likelihood is based, at least in part, on the calculated ratio.

According to some embodiments of the invention the determination of the likelihood is by thresholding.

According to some embodiments of the invention the method is executed for a plurality of biopsy samples of the same prostate gland. According to some embodiments of the invention the method comprises normalizing zinc level and epithelial glandular tissue concentration in each individual sample, respectively by a combined zinc level and a combined epithelial glandular tissue concentration.

According to some embodiments of the invention the method is executed for a plurality of biopsy samples of the same prostate gland. According to some embodiments of the invention the method comprises normalizing in each individual sample, zinc level, epithelial glandular tissue concentration, and the ratio between the zinc level and the epithelial glandular tissue concentration, respectively by a combined zinc level, combined epithelial glandular tissue concentration, and a combined ratio between the zinc level and the epithelial glandular tissue concentration.

According to some embodiments of the invention the method comprises using the zinc level and the epithelial glandular tissue concentration in the sample to calculate at least one biopsy parameter characterizing the prostate gland.

According to some embodiments of the invention the method comprises normalizing each of the at least one least one biopsy parameter by a respective biopsy population parameter characterizing a population of prostate glands.

According to some embodiments of the invention the population is annotated as a population of cancerous prostate glands. According to some embodiments of the invention the population is annotated as a population of benign prostate glands.

According to some embodiments of the invention the method comprises normalizing each of the at least one biopsy parameter by a respective biopsy population parameter characterizing a population of cancerous prostate glands, and normalizing each of the at least one biopsy parameter by a respective biopsy population parameter characterizing a population of benign prostate glands.

According to some embodiments of the invention the method comprises: accessing a computer-readable medium storing a library having a plurality of entries, each comprising annotation information of a particular population, and at least one biopsy population parameter characterizing the particular population; searching the library for an entry having a biopsy population parameter that best matches the biopsy parameter; and extracting annotation information from the found entry.

According to some embodiments of the invention the method comprises: accessing a computer-readable medium storing a library having a plurality of entries, each comprising annotation information of a particular population, and at least one biopsy population parameter characterizing the particular population; determining similarity between the biopsy parameter and biopsy population parameters of at least two entries; extracting annotation information from the at least two entries; and generating an output pertaining to the similarities and the extracted annotation information.

According to some embodiments of the invention annotation information of at least one entry comprises indication that a respective population is cancerous, and wherein annotation information of at least one entry comprises indication that a respective population is benign. According to some embodiments of the invention annotation information of at least one entry comprises indication that a respective population is cancerous and indication pertaining to a cancer grade of the respective population.

According to some embodiments of the invention the measurement of the zinc level and the measurement of the epithelial glandular tissue concentration is by X-Ray Fluorescence (XRF).

According to some embodiments of the invention the method is executed for a plurality of biopsy samples of the same prostate gland, thereby providing a plurality of likelihood values. According to some embodiments of the invention the method comprises determining a cancer grade of the plurality of biopsy samples, based on the plurality of likelihood values.

According to some embodiments of the invention the method the biopsy sample is a biopsy core.

According to some embodiments of the invention the method comprises generating output pertaining to a recommendation to extract an additional biopsy sample from the prostate gland, based on the likelihood. According to some embodiments of the invention the method comprises extracting an additional biopsy sample from the prostate gland responsively to the likelihood.

According to some embodiments of the invention the method is initially executed for no more than eight of biopsy samples of the same prostate gland. According to some embodiments of the invention the method comprises generating output pertaining to a recommendation to extract an additional biopsy sample from the prostate gland, based on the likelihood.

According to some embodiments of the invention the method is executed interactively with the biopsy.

According to some embodiments of the invention the method is executed before the biopsy sample undergoes any treatment or physical or chemical processing.

According to an aspect of some embodiments of the present invention there is provided a system for analyzing a biopsy sample containing tissue extracted from a prostate gland of a subject. The system comprising: an X-Ray Fluorescence (XRF) system configured for obtaining XRF data from the sample; and a data processor, configured to receive the XRF data and execute the method as delineated above and optionally and preferably as further detailed below.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
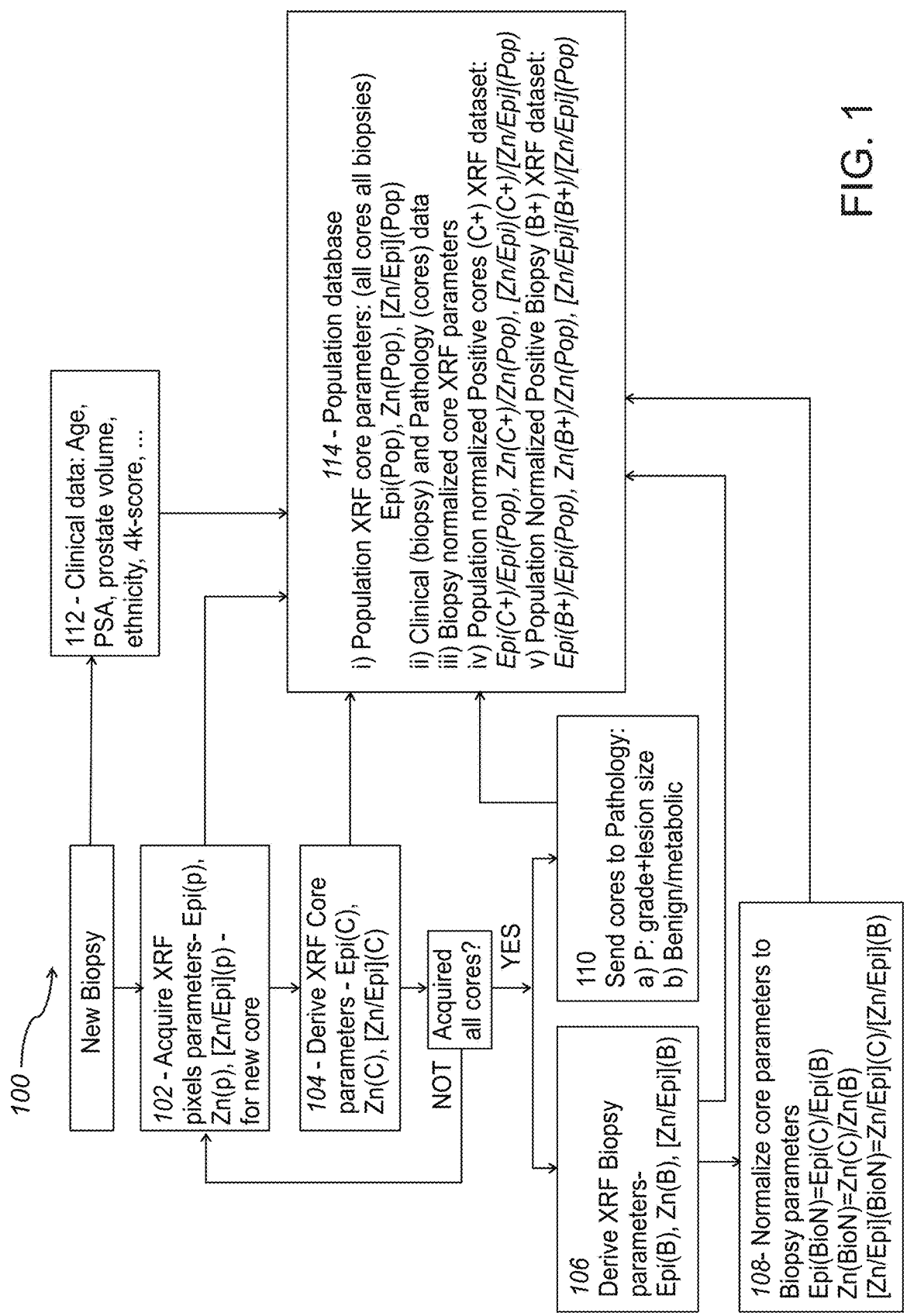
FIG. 1 is a flowchart of a method of population database generation and normalization according to embodiments of the present disclosure.

The present invention, in some embodiments thereof, relates to tissue analysis and, more particularly, but not exclusively, to a method and system for analyzing prostate biopsy.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some embodiments of the present invention provide diagnosis of prostate cancer during a biopsy procedure. The diagnosis can be provided immediately after the biopsy samples are removed from the patient (e.g., within less than an hour, or less than 50 minutes, or less than 40 minutes, or less than 30 minutes, or less than 20 minutes, or less than 10 minutes, or interactively during the biopsy).

In some embodiments of the present invention Zinc levels are measured in one or more pixels of a biopsy sample of a prostate tissue. The relative concentration and/or composition of epithelial glandular tissue (hereinafter "Epi") in the same one or more pixels of the biopsy sample is obtained. The Zn levels and the Epi relative concentrations are then used to determine whether cancerous lesions are present in the biopsy sample. Specifically, wherein a reduced Zn level combined with an elevated Epi measure is indicative of the presence of cancerous lesions.

In some preferred embodiments of the invention, the prostate tissue samples used for the Zn and Epi measurements are obtained from prostate biopsy cores.

In some preferred embodiments of the invention, the Zn levels and Epi relative concentrations are measured using an X-Ray Fluorescence (XRF) system.

Some embodiments of the present invention relate to the use of a population database of Zn Based Biopsy patients. The database can include statistical levels of Zn, Epi and Zn/Epi ratios for the population of all patients, and levels of Zn, Epi and Zn/Epi ratios for positive PCa biopsy cores in the population, optionally and preferably sorted according to grade and lesion size. The database can further include joint levels of Zn, Epi and Zn/Epi ratios for positive PCa prostates in the population, optionally and preferably stratified according to grade, and the joint levels of Zn, Epi and Zn/Epi ratios for negative (e.g., benign) prostates in the population. Optionally and preferably the database also includes joint levels of Zn, Epi and Zn/Epi ratios for metabolic prostates (e.g, prostatitis).

The classification and diagnosis of the biopsy samples (e.g., cores) of a given prostate, and optionally and preferably also of the given prostate itself, can be based according to some embodiments of the present invention on the normalization of the values of Zn, Epi and Zn/Epi ratios for each sample (e.g., core) to the corresponding values for the prostate to which the samples (e.g., cores) belong ("Biopsy Normalization"). The classification and diagnosis can also be based on the normalization of the values of Zn, Epi and Zn/Epi cores for each sample (e.g., core) to the values of the population of previously diagnosed prostates ("Population Normalization"), and/or to a sub-set of the population of previously diagnosed prostates ("Mid Population normalization"). Optionally and preferably the classification and diagnosis is also based on Population Normalization and Mid-Population Normalization of the values of Zn, Epi and Zn/Epi of the prostate itself.

In some embodiments of the present invention a risk assessment of the patient is established, separately or together with the aforementioned classification and diagnosis. For example, if there are positive cores, the risk assessment can indicate the number of positive cores found, and the grade and lesion extension of the tumor for each identified positive core and the corresponding values, relative to the population database levels ("Relative Values"), of Zn and epithelial for each core. The risk assessment can also indicate the cancerous positivity grade of the prostate and the Relative Values of Zn and epithelial for the prostate. If no positive cores are found, the risk assessment can indicate the prostate negativity grade and the Relative Values of Zn and epithelial for the prostate. Indications for treatment options can be provided for example, based on the prostate levels of Zn and epithelial normalized to population levels.

A database including the patient clinical data and the XRF data for the population of scanned prostates can be accessed, optionally and preferably immediately after the biopsy samples are removed from the patient (e.g., within less than an hour, or less than 50 minutes, or less than 40 minutes, or less than 30 minutes, or less than 20 minutes, or less than 10 minutes, or interactively during the biopsy), to perform the Population or Mid Population Normalization for any particular prostate under examination, and optionally and preferably also to update the Population Data following examination. In some embodiments of the present invention cross-normalization of the data from all systems is performed.

Some embodiments of the present invention thus generate Biomarker Information indicative of the positivity (e.g., cancerous level), or negativity (e.g., benign, pre-cancerous level), of a prostate under examination. Some embodiments of the present invention establish risk assessment and/or prognosis for the patient under examination based on the Biomarker Information, and optionally and preferably additional risk factors derived during the biopsy procedure, such as, but not limited to, number, location, and/or grade of the positive cores found.

The present embodiments also provide a biopsy guidance technique. In these embodiments, a number of cores are removed from predetermined initial sites in the prostate, wherein the predetermined initial sites are selected from a predetermined biopsy site map. The Zn and Epi in the initial cores are measured, optionally and preferably immediately after their removal. The Zn and Epi measurements are then combined to classify each of the initial cores as one of a cancer positive core or a cancer negative core, and the prostate is classified as either a cancer positive prostate or a cancer negative prostate based on the classifications of the individual cores. For example, the prostate is classified as a cancer positive prostate when at least one of the initial cores is a cancer positive core, and as a cancer negative prostate when none of the of the initial cores is a cancer positive core. A guidance of additional sites for removal of additional cores is then provided, wherein the guidance comprises a positive guidance for the cancer positive prostate, and a negative guidance for the probably cancer negative prostate.

At least part of the operations described herein can be implemented by a data processing system, e.g., a dedicated circuitry or a general purpose computer, configured for receiving data and executing the operations described below. At least part of the operations can be implemented by a cloud-computing facility at a remote location.

Computer programs implementing the method of the present embodiments can commonly be distributed to users by a communication network or on a distribution medium such as, but not limited to, a floppy disk, a CD-ROM, a flash memory device and a portable hard drive. From the communication network or distribution medium, the computer programs can be copied to a hard disk or a similar intermediate storage medium. The computer programs can be run by loading the code instructions either from their distribution medium or their intermediate storage medium into the execution memory of the computer, configuring the computer to act in accordance with the method of this invention. During operation, the computer can store in a memory data structures or values obtained by intermediate calculations and pulls these data structures or values for use in subsequent operation. All these operations are well-known to those skilled in the art of computer systems.

Processing operations described herein may be performed by means of processer circuit, such as a DSP, microcontroller, FPGA, ASIC, etc., or any other conventional and/or dedicated computing system.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

Figure 11:
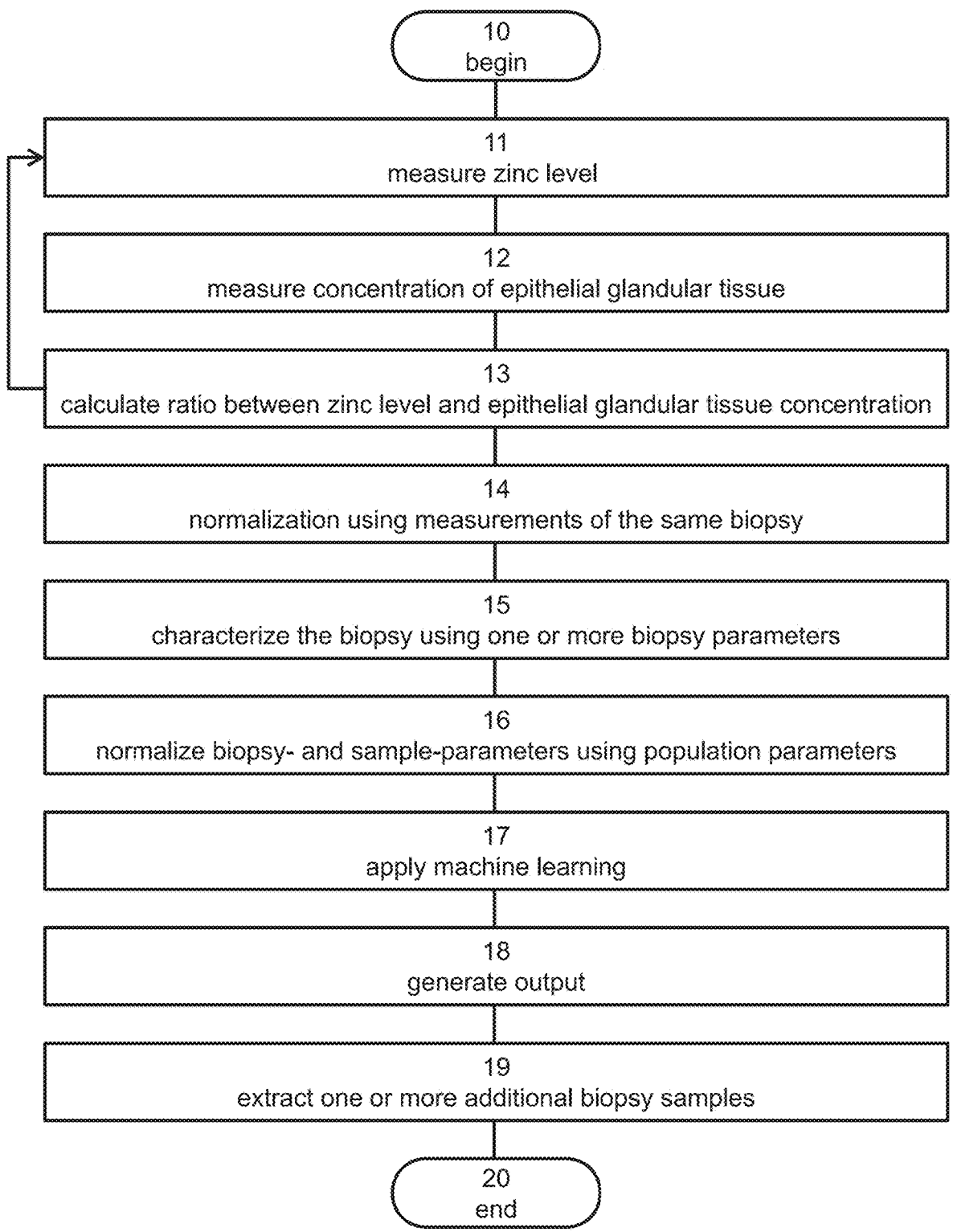
FIG. 11 is a flowchart diagram of a method suitable for analyzing a biopsy sample according to some embodiments of the present invention.

Referring now to the drawings, FIG. 11 is a flowchart diagram of a method suitable for analyzing a biopsy sample according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The biopsy sample contains tissue extracted from a prostate gland of a subject. The tissue can be extracted by core biopsy. In core biopsy, a core or fragment of tissue is obtained by a core biopsy needle. The extraction of samples can be performed using robotic arms as known in the art. The biopsy can be TRUS biopsy or TP biopsy. Then method of the present embodiments can be performed interactively during the biopsy.

The method begins at 10, optionally and preferably before the biopsy sample underwent any treatment, or physical or chemical processing, e.g., handling, placing in a fixing agent (e.g., formalin), or any other operation that may alter the zinc level or concentration of epithelial glandular tissue in the sample. The method optionally and preferably begins immediately after the biopsy samples are removed from the patient (e.g., within less than an hour, or less than 50 minutes, or less than 40 minutes, or less than 30 minutes, or less than 20 minutes, or less than 10 minutes. The method optionally and preferably continues to 11 at which a zinc level in the sample is measured, and to 12 at which a concentration in the sample of epithelial glandular tissue is measured. The preferred technique for measuring both the zinc level and the concentration of the epithelial glandular tissue is by X-Ray Fluorescence (XRF).

XRF is an analytical method widely used for analysis of trace elements in various matrices. Biological samples such as tissues can be analysed intact by XRF without sample processing. In XRF, the analysed tissue may be exposed to a low radiation dose of X-rays or low energy gamma rays from an X-ray tube or an isotopic radioactive source, which as described herein are non-limiting examples of irradiation systems and/or may form a component of such a system. This radiation causes the excitation of the atoms present in the tissue, which in turn decay by emission of characteristic fluorescent X-rays. These characteristic X-rays emitted from the sample are detected and counted by a detector. The intensity of these X-rays is directly proportional to the concentration of the elements inside the tissue. In the case of Zinc, the characteristic fluorescent X-ray energies are 8.6 and 9.6 keV. The limits of detection are typically below one part per million.

Typically, a pixelated XRF map of the sample is generated, and a local zinc level is extracted for each pixel of XRF map, to provide a plurality of local zinc levels, one local zinc level per pixel of the XRF map. The zinc level of the sample can then be obtained by averaging over the local zinc levels. Preferably, one or more additional statistical measures of the zinc level are also calculated. These can include statistical measures of location and/or statistical measures of spread. For example, in some embodiments of the present invention a statistical moment of the zinc level (e.g., standard deviation) is calculated, and in some embodiments of the present invention a statistical measure of location (in addition to the average) is calculated (e.g., median, mode, etc.).

The X-Ray spectrum is not only a measure of the geometry and mass along the sample, but is also influenced by the molecular composition and/or the changes in density along the sample. XRF provides a fluorescence energy spectrum from which concentration of very low levels of chemical elements can be determined. The XRF spectrum also incorporates scattering components comprising an inelastic (Compton) scattering spectrum, and an elastic (Rayleigh) scattering component. The prostatic tissue is mainly composed of two general types of tissue: stroma and epithelial. The XRF spectrum can be used to differentiate between these types of tissues. The inventor found that by analyzing the contributions of the two components to the scattering the concentration of epithelial glandular tissue can be found. It was unexpectedly found by the Inventor that the Rayleigh component of the XRF contains information pertaining to differences between the different molecular compositions in the sample, and that this component can be used, at least in part, for estimating the concentration of the epithelial glandular tissue.

According to some embodiments of the present invention the Rayleigh component is obtained from the XRF spectrum by indirect calculation. This is advantageous since the Rayleigh component is typically small compared to the Compton component, and so it may be difficult to obtain it directly from the XRF spectrum. In experiments performed by the Inventor it was found that it advantage to subtract the Compton component of the XRF spectrum from the combined contribution to the scattering of both the Compton and the Rayleigh components of the spectrum, and correlate the result of this subtraction to the epithelial glandular tissue concentration. Thus, denoting the XRF sub-spectrum resulting from Compton scattering by $S_C$, the XRF sub-spectrum resulting from Rayleigh scattering by SR, and XRF sub-spectrum resulting from both Compton scattering and Rayleigh scattering by $S_{CR}$, the measurement 12 of the concentration of epithelial glandular tissue is done by calculating the difference $S_{CR}-S_C$ and determining the epithelial glandular tissue concentration based on this difference.

In some embodiments of the present invention the difference $S_{CR}-S_C$ is expressed in terms of a fraction or a percentage of the XRF sub-spectrum resulting from Compton scattering, $S_C$. This is advantageous because $S_C$ also correlates with the volume of the sample, and so normalizing the difference $S_{CR}$-$S_C$ by $S_C$ reduces or eliminates the effect of the sample size on the calculated value. Thus, in some embodiments of the present invention the epithelial glandular tissue concentration is defined as a function, more preferably a linear function, of the ratio ($S_{CR}$-$S_C$)/$S_C$. For example, in some embodiments of the present invention the linear function has a coefficient 1 and an offset 0, in which case the epithelial glandular tissue concentration is defined as the ratio ($S_{CR}$-$S_C$)/$S_C$ itself.

When a pixelated XRF map of the sample is generated, a local epithelial glandular tissue concentration is extracted for each pixel of XRF map to provide a plurality of local epithelial glandular tissue concentrations, one local epithelial glandular tissue concentration per pixel of the XRF map. The epithelial glandular tissue concentration of the sample can then be obtained by averaging over the local epithelial glandular tissue concentrations. Preferably, one or more additional statistical measures of the epithelial glandular tissue concentration are also calculated. These can include statistical measures of location and/or statistical measures of spread. For example, in some embodiments of the present invention a statistical moment of the epithelial glandular tissue concentration (e.g., standard deviation) is calculated, and in some embodiments of the present invention a statistical measure of location (in addition to the average) is calculated (e.g., median, mode, etc.).

The Inventor unexpectedly found that a cancerous biopsy sample from a prostate typically contains high concentration of epithelial glandular tissue and low zinc levels. The Inventor therefore concluded that the zinc level and the epithelial glandular tissue concentration can be used together for characterizing the likelihood that a biopsy sample from the prostate is cancerous. For example, the likelihood can be by thresholding, wherein when the zinc level is below a predetermined zinc level threshold and the epithelial glandular tissue concentration is above a predetermined concentration threshold the sample is likely to be cancerous.

The method optionally and preferably continues to 13 at which a ratio between the measured zinc level and epithelial tissue concentration is calculated. When a pixelated XRF map of the sample is generated, the ratio is preferably calculated for each pixel of the XRF map, to provide a plurality of local ratio values, one local ratio value per pixel of the XRF map. Thereafter, the local ratio values are processed statistically. Specifically, in these embodiments, each local ratio is calculated as a ratio between a respective local zinc level and a respective local epithelial glandular tissue concentration. The ratio between the zinc level and the epithelial tissue concentration of the sample can then be obtained by averaging over the local ratios. Preferably, one or more additional statistical measures of the ratio are also calculated. These can include statistical measures of location and/or statistical measures of spread. For example, in some embodiments of the present invention a statistical moment of the ratio (e.g., standard deviation) is calculated, and in some embodiments of the present invention a statistical measure of location (in addition to the average) is calculated (e.g., median, mode, etc.).

The Inventor found that when a biopsy sample of a prostate is benign there is a linear correlation between the zinc level and the concentration of epithelial tissue. The linear relationship was confirmed experimentally by comparing visual counts of epithelial cells on pathology slides with epithelial tissue concentration obtained by XRF. It was found that typically benign prostates have higher correlation coefficient and/or a higher zinc baseline.

Since the likelihood that the sample is cancerous increases with increased concentration of epithelial glandular tissue and with reduced zinc level, the Inventor found that it is advantageous to calculate the ratio of zinc level to epithelial glandular tissue concentration, since such ratio can be used as a biomarker for classification of a sample as cancerous or benign, wherein a lower ratio is indicative of higher likelihood for a cancerous sample, and a lower ratio is indicative of higher likelihood for a cancerous sample. The ratio between the zinc level and the concentration of epithelial glandular tissue is referred to herein as Zn/Epi.

Thus, a thresholding procedure can also be applied to the ratio Zn/Epi, wherein when the ratio Zn/Epi zinc is below a predetermined ratio threshold the sample is likely to be cancerous.

From 13 the method optionally and preferably loops back to 11 and executes 11, 12, and optionally and preferably also 13, for another biopsy sample of the same prostrate. The loopback is optionally and preferably repeated until all the samples extracted from the same prostate gland have been processed, so that each sample is associated with one or more sample-parameters. For example, when there are N samples in a single biopsy procedure, the operations 11, 12 and optionally 13 are repeated N times. Typically, N equals from about 8 to about 15. The sample-parameter(s) are optionally and preferably sample-parameters that are calculated statistically as further detailed hereinabove. For example, each sample can be associated with a zinc level Zn (preferably obtained by averaging local zinc levels over the pixels of XRF map, as further detailed hereinabove), and with a concentration Epi of epithelial glandular tissue (preferably obtained by averaging local epithelial glandular tissue concentrations over the pixels of XRF map, as further detailed hereinabove). Alternatively or additionally, each sample can be associated with a ratio Zn/Epi (preferably obtained by averaging local ratios over the pixels of XRF map, as further detailed hereinabove). Alternatively or additionally, each sample can be associated with one or more statistical measures of location and/or statistical measures of spread, for one or more of the zinc level, the epithelial glandular tissue concentration, and the ratio Zn/Epi.

The method optionally and preferably continues to 14 at which one or more of the sample-parameters are normalized by a respective combined sample-parameter obtained from the measurements executed for samples extracted from the same prostate. For example, the zinc level and epithelial glandular tissue concentration in each individual sample can be normalized, respectively by a combined zinc level and a combined epithelial glandular tissue concentration obtained from the measurements executed for samples extracted from the same prostate. The normalization 14 optionally and preferably also comprises normalizing the Zn/Epi ratio associated with each sample by a combined Zn/Epi ratio obtained from the measurements executed for the samples extracted from the same prostate. In some embodiments of the present invention the combined zinc level is the average of all the Zn values (N Zn values in the above example), the combined epithelial glandular tissue concentration is the average of all the Epi values, and the combined Zn/Epi ratio is the average of all the Zn/Epi ratios. Other combined zinc level, other combined epithelial glandular tissue concentrations, and other combined Zn/Epi ratios are also contemplated.

When a pixelated XRF map of the sample is generated, the normalization 14 is preferably executed by calculating a biopsy normalization factor for the respective sample-parameter, and dividing each respective sample-parameter by the calculated biopsy normalization factor. For example, the normalization of the zinc level can be executed by averaging the local zinc levels of all the pixels of all the samples, to provide a biopsy zinc normalization factor. Alternatively, the biopsy zinc normalization factor can be obtained by performing a weighted average of the zinc levels of all the samples using the number of pixels in each sample as a weight for the weighted average. The zinc level of each sample can then be divided by the biopsy zinc normalization factor to provide a normalized zinc level for the respective sample. A similar procedure can be performed mutatis mutandis for other sample-parameters, e.g., the epithelial glandular tissue concentration and/or the ratio between the zinc level and the epithelial glandular tissue concentration, and/or any of the statistical measures calculated for each sample.

In some embodiments of the present invention the method continues to 15 in which an overall zinc level, an overall epithelial glandular tissue concentration, and and/or an overall ratio Zn/Epi is calculated for the plurality of samples extracted during the same biopsy procedure, thereby providing one or more biopsy parameters that characterize the biopsy. These overall values are referred to herein as a biopsy Zn value, a biopsy Epi value, and a biopsy Zn/Epi value, respectively. Each overall value can be calculated by averaging the respective parameter over all the pixels of all the samples, or alternatively by calculating a weighted average of each sample-parameter over all the samples, using the number of pixels in each sample as a weight for the weighted average. The present embodiments also contemplated calculating, in a similar way, an overall value for each statistical measure calculated for the samples.

In some embodiments of the present invention the method proceeds to 16 at which the biopsy parameters are normalized by respective biopsy population parameters characterizing a population of prostate glands. The biopsy population parameters are typically of the same type as the biopsy parameters calculated at 15. Specifically, when the biopsy parameter is a biopsy Zn value, it is normalized to a biopsy population parameter which is a biopsy population Zn value calculated by combining (e.g., averaging) the individual biopsy Zn values of at least a portion of the prostate glands of the population; when the biopsy parameter is a biopsy Epi value, it is normalized to a biopsy population parameter which is a biopsy population Epi value calculated by combining (e.g., averaging) the individual biopsy Epi values of at least a portion of the prostate glands of the population, and when the biopsy parameter is a biopsy Zn/Epi value, it is normalized to a biopsy population parameter which is a biopsy population Zn/Epi value calculated by combining (e.g., averaging) the individual biopsy Zn/Epi values of at least a portion of the prostate glands of the population.

The present embodiments also contemplate using the biopsy population parameters for separately normalizing the sample-parameter(s) of the individual samples of the biopsy. In these embodiments when the sample-parameter is a Zn value, it is normalized to the biopsy population Zn value, when the sample-parameter is a Epi value, it is normalized to the biopsy population Epi value, and when the sample-parameter is a Zn/Epi value, it is normalized to the biopsy population Zn/Epi value.

The biopsy population parameter(s) can be obtained by accessing a computer-readable medium storing the biopsy population parameters. A preferred procedure for preparing biopsy population parameters that can be used in accordance with some embodiments of the present invention is provided in the Examples section that follows.

The population that is characterized by the biopsy population parameter(s) is optionally and preferably annotated population.

The term "annotated population" refers to a population which is associated with annotation information. The annotation information can be stored together from the biopsy population parameter(s) (e.g., in the same file on a computer readable medium). The annotation information is preferably global annotation wherein the entire population is identified as corresponding to a specific condition. Thus, for example, the annotation information can pertain to the presence, absence or level of prostate cancer in the population.

In some embodiments of the present invention the population is annotated as a population of benign prostate glands. In these embodiments, the normalization at 16 allows the method to assess the similarity between the prostate gland from which the biopsy samples were extracted, and the benign prostate glands in the population. When a high degree of similarity is found, the method can determine that prostate gland under analysis is likely to be benign.

In some embodiments of the present invention the population is annotated as a population of cancerous prostate glands. In these embodiments, the normalization at 16 allows the method to assess the similarity between the prostate gland from which the biopsy samples were extracted, and the prostate glands in the population. When a high degree of similarity is found, the method can determine that prostate gland under analysis is likely to be cancerous.

In some embodiments of the present invention the population is annotated as a population of cancerous prostate glands with a specific cancer grade or a specific range of cancer grade. In these embodiments, the normalization at 16 allows the method to determine whether the cancer grade of the prostate gland from which the biopsy samples were extracted is the same as the grade of the prostate glands in the population.

The present disclosure contemplate embodiments in which the method accesses a computer-readable medium storing a library having a plurality of entries, each entry comprising annotation information of a particular population (e.g., a population of benign prostate glands, a population of cancerous prostate glands, a population of cancerous prostate glands with a specific cancer grade or a specific range of cancer grade), and one or more biopsy parameters characterizing the respective population. The method can then repeat 16 a plurality of times each time with respect to the population parameter(s) of a different library entry, and search for the entry in which the population parameter(s) best match the biopsy parameter(s) calculated at 15. The method can then extract the annotation information of the found entry and use it to determine the likelihood that the prostate is cancerous. When the annotation information of the found entry includes a cancer grade, the method can also determine the cancer grade of the prostate under analysis.

Also contemplated are embodiments in which the method determines similarity between the biopsy parameter(s) as provided at 15 and the biopsy population parameters of two or more entries of the library. These embodiments are useful for characterizing the prostate gland under analysis in a more detailed manner, where the method can determine the level of similarity between the biopsy parameter(s) and the biopsy population parameters of a first population, the level of similarity between the biopsy parameter(s) and the biopsy population parameters of a second population, and so on. For example, the method can determine the level of similarity between the biopsy parameter(s) and the biopsy population parameters of a benign population, as well as the level of similarity between the biopsy parameter(s) and the biopsy population parameters of a cancerous population.

In some embodiments of the present invention a machine learning procedure is applied 17 to the biopsy- and/or sample-parameters. This can be done by accessing a computer readable medium storing a machine learning procedure, which is preferably trained for predicting the likelihood for a prostate gland to be cancerous and/or for predicting the likelihood for a biopsy sample extracted from prostate gland to be cancerous.

As used herein the term "machine learning" refers to a procedure embodied as a computer program configured to induce patterns, regularities, or rules from previously collected data to develop an appropriate response to future data, or describe the data in some meaningful way.

Representative examples of machine learning procedures suitable for the present embodiments, include, without limitation, clustering, association rule algorithms, feature evaluation algorithms, subset selection algorithms, support vector machines, classification rules, cost-sensitive classifiers, vote algorithms, stacking algorithms, Bayesian networks, decision trees, neural networks, convolutional neural networks, instance-based algorithms, linear modeling algorithms, k-nearest neighbors (KNN) analysis, ensemble learning algorithms, probabilistic models, graphical models, logistic regression methods (including multinomial logistic regression methods), gradient ascent methods, singular value decomposition methods and principle component analysis. In some embodiments of the present invention the machine learning procedure is a deep learning procedure.

A machine learning procedure can be trained according to some embodiments of the present invention by feeding a machine learning training program with sample-parameters and biopsy-parameters extracted from a cohort of prostate gland, for which characterizations with respect to malignancy or benignancy are known, for example, by from pathology investigation. Once the parameters are fed, the machine learning training program generates a trained machine learning procedure which can then be used without the need to re-train it.

For example, when it is desired to employ deep learning, a machine learning training program adjusts the connection strengths and threshold values among neurons and/or layers of an artificial neural network, so as to produce an output that resembles as much as possible the cohort's known characterizations with respect to benignancy or malignancy and optionally and preferably cancer grade. When the neural network is a convolutional neural network (CNN), a machine learning training program adjusts convolutional kernels and bias matrices of the CNN so as to produce an output that resembles as much as possible the cohort's known characterizations with respect to benignancy or malignancy and optionally and preferably cancer grade. The final result of the machine learning training program in these cases is an artificial neural network having an input layer, at least one, more preferably a plurality of, hidden layers, and an output layer, with a learn value assigned to each component (neuron, layer, kernel, etc.) of the network. The trained artificial neural network receives the biopsy- and/or sample-parameters at its input layer and provides the likelihood that the sample and/or entire prostate is cancerous at its output layer.

In some embodiments of the present invention the trained machine learning procedure provides the likelihood that the sample and/or entire prostate is cancerous, and, in case of malignancy of the prostate also provides the grade of the cancer.

At 18, an output is generated. The output can be displayed on a display device or transmitted to a computer readable medium. The output can be based on a comparison between the sample- and/or biopsy-parameters to the biopsy population parameters of an annotated database, and/or by applying the machine learning procedure. The output can include indication pertaining to the likelihood that a particular biopsy sample (e.g., a particular biopsy core) is cancerous. The output can include indication pertaining to the likelihood that the entire prostate gland is cancerous and optionally and preferably also indication pertaining to the cancer grade (e.g., based on the biopsy population parameter(s), as further detailed hereinabove). The output can also include a recommendation to extract one or more additional biopsy samples from the prostate gland (for example, when the biopsy parameters obtained at 15 are inconclusive as to the cancer grade).

It is appreciated that the method can provide more than one output, and can also provide preliminary output which is thereafter updated. For example, the method can provide a preliminary output describing the malignancy of a particular sample, before accessing the population database at 16 (e.g., immediately after 14). Following the normalization 16, the normalized parameters can be compared to the annotated database and/or be fed to the machine learning procedure, and the generated output can be updated based on the comparison and/or output from the machine learning procedure. As a representative example, consider a sample of a prostate under analysis for which the Zn/Epi value is low. A preliminary output can be that this sample is likely to be cancerous. However, following a comparison to an annotated database, it may be determined that the prostate under analysis belongs to a sub-population of benign prostates for which the Zn/Epi values are relatively low, and that the Zn/Epi value obtained for the particular sample of the prostate under analysis is within the norm of this sub-population. In this case, the preliminary output is replaced with a new output indicating that sample is unlikely to be cancerous.

In some embodiments of the present invention the method proceeds to 19 at which one or more additional biopsy samples are extracted from the prostate, thereby increasing the overall number of samples in the biopsy procedure. Operation 19 is typically executed responsively to the output generated at 18. Specifically, operation 19 is optionally and preferably executed when the output 18 includes a recommendation to extract one or more additional biopsy samples from the prostate gland.

The method ends at 20.

The method 10 of the present embodiments is useful for reducing the number of unnecessary biopsy samples that are extracted, improve the accuracy of the analysis, and reduce the analysis time. For example, the method 10 can be initially applied to a relatively small (e.g., 4-6) number of biopsy samples, and an initial likelihood that prostate is cancerous is determined, for example, by determining the number of samples which are likely to be cancerous. Preferably, at the initial stage, no samples are extracted from the line adjacent to the prostate's base (the upper region of the prostate close to the urethra, see FIG. 7). For example, samples can be extracted from the line adjacent to the prostate's apex (e.g., along the path from LL4 to RL4 in FIG. 7), from the upper mid-gland-line of the prostate (e.g., along the path from LL2 to RL2 in FIG. 7), and from the lower mid-gland-line of the prostate (e.g., along the path from LL3 to RL3 in FIG. 7).

The initial likelihood provides feedback to the practitioner to either end the procedure (e.g., if no sample was found to be cancerous or likely to be cancerous), or, conversely, to extract more samples from the prostate (e.g., if one or more samples is likely to be cancerous). If initial likelihood provides feedback to extract more samples, the sites from which the additional samples are to be extracted can be determined by identifying the sites from which the samples that are likely to be cancerous have been extracted. For example, the additional biopsy samples can be extracted at locations near those samples. The extraction of samples can be typically performed using robotic arms as used in MRI guided biopsies.

Figure 12:
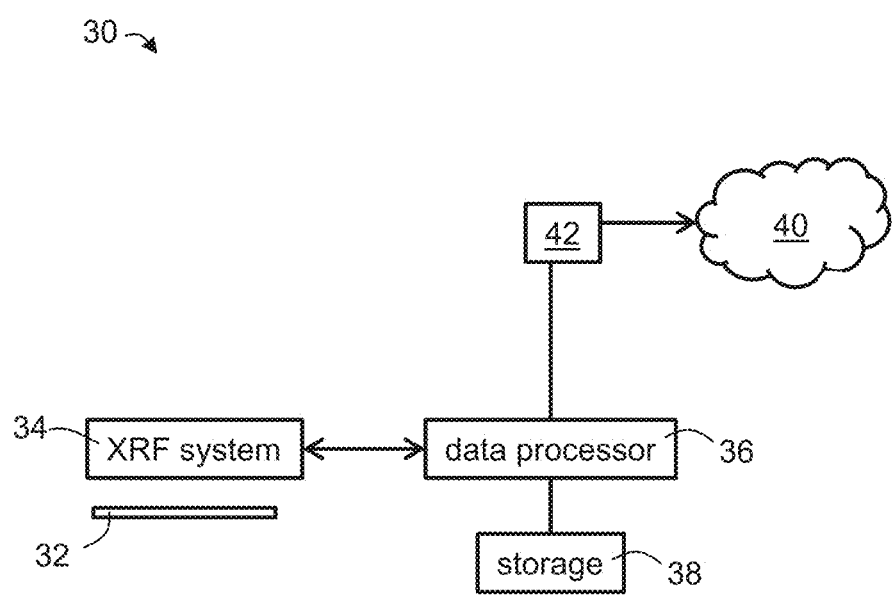
FIG. 12 is a schematic illustration of a system for analyzing a biopsy sample containing tissue extracted from a prostate gland of a subject, according to some embodiments of the present invention.

Reference is now made to FIG. 12 which is a schematic illustration of a system 30 for analyzing a biopsy sample 32 containing tissue extracted from a prostate gland of a subject, according to some embodiments of the present invention. System 30 comprises an XRF system 34, that obtains XRF data from the sample 32. The XRF data optionally and preferably include zinc level data (Zn), epithelial glandular tissue concentration data (Epi) and the ratio Zn/Epi obtained as further detailed hereinabove. System 30 further comprises a data processor 36, configured to receive the XRF data from XRF system 34 and analyze the data to determine the likelihood that the sample 32 is cancerous, as further detailed hereinabove. Typically, processor 36 is configured to execute selected operations of method 10. Processor 36 can further comprise a computer-readable storage medium 38. Medium 38 is preferably non-transitory storage medium storing computer code instructions for executing the method of the present embodiments, and processors 36 executes these code instructions. The code instructions can be run by loading the code instructions into the execution memory of processors 36. Storage medium 38 can also store one or more databases of populations of prostates as further detailed hereinabove. Storage medium 38 can store a trained machine learning procedure as further detailed hereinabove. Also contemplated are embodiments in which the databases of populations of prostates and/or trained machine learning procedure are stored in a cloud storage facility 40, in which case processor 36 communicates with cloud storage facility 40 over a network 42, such as a local area network (LAN), a wide area network (WAN) or the Internet. Cloud storage facility 40 can in some embodiments be a part of a cloud computing resource of a cloud computing facility in which case at least some of the operations of the method are executed by the cloud computing facility.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein "real-time" means immediately after the biopsy samples are removed from the patient (e.g., within less than an hour, or less than 50 minutes, or less than 40 minutes, or less than 30 minutes, or less than 20 minutes, or less than 10 minutes).

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Known modalities for analyzing biopsy samples do not provide real-time, on-the-spot diagnostic feedback and guidance to the urologist during the biopsy. Therefore, it is still necessary to wait one or more weeks after the biopsy for the pathology diagnostic, and there is no possibility of actual improvement in the accuracy of the biopsy beyond the intrinsic accuracy of the MRI, which is limited for the cases of small lesions/grades.

Furthermore, current pre-biopsy screening of PCa, based on prostate-specific-antigen (PSA) and/or other blood or urine tests, together with other factors, including age, race, family history and Digital Rectal Examination (DRE), has poor specificity and sensitivity for patients with low PSA (<10 ng/ml). Therefore, MRI imaging prior to a first TRUS biopsy is currently recommended for patients with high PSA, typically higher than 10 ng/ml and according to age and other factors as mentioned above. MRI imaging and Fusion is currently routinely recommended for repeat biopsies.

Nevertheless, a substantial proportion of the first TRUS biopsies are still performed without previous MRI imaging and Fusion. The cancer detection rate (CDR) and false negative rate (FN) of unguided TRUS biopsy for 1st biopsy patients are poor, respectively CDR around 30% and FN around 25%.

Additionally, there is a practical limit to the number of cores to be removed due to the discomfort and potential side-effects to the patient, like bleeding and infections, related to higher cores removal.

Among the reasons for such poor diagnostic performance are the poor sensitivity and specificity of the PSA blood test for screening, the fact that the standard TRUS biopsy is blind and random and the fact that there is no diagnostic feedback and guidance to the practitioner during the biopsy session itself.

Additionally, the diagnosis is provided only days after the biopsy, i.e. there is no feedback or guidance to the practitioner during the biopsy that could alter the scheme of removal of cores to avoid false negatives or to increase the cancer detection rate.

Additionally, there is no prostate biomarker information derived during the standard TRUS biopsy and the pathology diagnosis is targeted at the morphology of the epithelial cells in the prostate biopsy tissue sample.

Additionally, patient cancer risk assessment and treatment options following 1st TRUS biopsy are not decisive in the majority of cases and require further diagnostic steps, according to the pathology report and subsequent blood or genetic tests following the biopsy. Accordingly, in more than 20% of the cases, patients are directed at repeat TRUS biopsies, typically saturated biopsies where more cores (18 or more) are removed.

The technique of the present embodiments proves accurate autonomous real-time guidance and is capable of providing on-the-spot preliminary diagnosis based on prostate biomarker information. The technique of the present embodiments thus removes the current blindness in the first standard TRUS biopsy, achieves much improved sensitivity and specificity (e.g., lower false negatives and higher true positives), and provides a biomarker-based patient cancer risk prognosis. The technique of the present embodiments can optionally and preferably complement pre-biopsy guidance, such as the biopsy guidance provided by MRI, to provide both higher positive yields and higher sensitivity for the MRI Fusion biopsy.

The sole use of Zn as a biomarker of prostate cancer (PCa) in a biopsy location (see, Simon et al, supra) did not provide the sensitivity and specificity necessary for real-time diagnosis and guidance to achieve very low levels of false negatives in the biopsy. The technique of the present embodiments provides accurate real time diagnostic and can also provide guidance feedback to the Urologist during the biopsy procedure itself based on Zn and one or more additional PCa biomarkers.

The following definitions and abbreviations are used in the disclosure:

PCa—Prostate cancer.
XRF—X-ray fluorescence.
Epi—XRF derived levels of epithelial gland density.
Zn—XRF derived levels of Zn concentration.
XRF Parameters—XRF derived levels of mean and σ of Epi, Zn and Zn/Epi.
Population Data—XRF Parameters corresponding to a population of biopsies. The levels of Epi, Zn and Zn/Epi for each Pixel in a Core, for all the Cores in a Prostate (the "Biopsy") and for all the Prostates previously scanned with the XRF system (the "Population") constitute, together with the Pathology and Clinical data for each core in each prostate.
Positive Biopsies Population Data—XRF Parameters corresponding to a sub-set of the Population Data for which Biopsies have been classified positive by pathology.
Positive Cores Population Data—XRF parameters corresponding to a sub-set of the Population Data for which cores have been classified positive by pathology.
Biopsy Dataset—XRF Parameters corresponding to a single given biopsy.
Core Dataset—XRF Parameters corresponding to each of the cores removed in a biopsy.
Pixel Data—XRF Parameters corresponding to each of the pixels within each of the cores.
Pathology Data—pathology classification of each biopsy core as benign, PCa or metabolic.
Biopsy Class—XRF Parameters corresponding to a group of prostates belonging to the same biopsy pathology classification.
Core Class—XRF Parameters corresponding to a group of cores belonging to the same core pathology classification.
PopN—Normalization of XRF Parameters relative to the Population Data.
BioN—Normalization of XRF Core Parameters relative to the Biopsy XRF parameters for the prostate they belong to.
P—Positive; N—Negative; FP—False Positive; FN—False Negative; TP—True Positive; TN—True Negative.
Prostate Peripheral Zone—The region on the prostate closer to the Rectum.
Prostate Base—The upper region of the prostate closer to the Urethra.
Prostate Apex—The lower region of the prostate.
Zn Based Biopsy—A prostate biopsy intended at establishing the levels of Zn and epithelial glands ("Biomarker Information"), both along each core removed from the prostate as well as for the prostate as a whole, measured or derived during the biopsy.
"Zn Depletion"—corresponds to local levels of Zn statistically significantly lower than the normal (i.e. non-cancerous) levels relative to the local Epithelial levels.
"Core PCa classification"—Determining if a core is positive, and establishing its grade and lesion size based on the Zn and Epi Biomarker Information, e.g. the mean level of Zn depletion and the level of Zn depletion along the core.
"Prostate PCa classification"—the use of the Zn Based Biopsy Biomarker Information for the prostate, such as, but not limited to, the statistics for all the pixels and cores removed, for establishing whether a prostate is PCa Positive (P) or Benign (N) and the grade of the prostate, if positive.

"Positivity and Negativity of prostates"—(i) for a positive prostate, as established by the presence of positive cores and their grades, the positivity represents whether the PCa level is clinically significant or not, for example, medium to high PCa risk or low to medium PCa risk; (ii) for a negative prostate, for which no PCa cores were found during the biopsy, the negativity or positivity indicates whether the prostate Zn depletion levels are lower or higher than normal (benign) respectively, therefore indicating whether the PCa risk is very low or low respectively.

The present Example describes the combined use of a quantity—"Epi"-associated to the amount of epithelial glands along the core and derived from the XRF data, directly or indirectly, together with the Zn content information, to achieve high sensitivity and specificity in the real time determination of PCa lesions in prostatic tissue, typically in prostate biopsy cores.

The X-Ray spectrum measured with an XRF system is not only a measure of the geometry and mass along the sample, but is also influenced by the (molecular) composition and/or the changes in density along the sample. XRF provides a fluorescence energy spectrum from which can be derived concentration measurements of very low levels of chemical elements. The XRF spectrum also incorporates scattering components comprising an inelastic (Compton) scattering spectrum and an elastic (Rayleigh) scattering component.

The prostatic tissue is mainly composed of two general types of tissue: stroma and epithelial—which define a mean density for non-cancerous conditions and relative amounts of each tissue type. When there is a cancerous process, there is an increase in the stiffness and density of the tissue at the cancer site, therefore the Compton count for this site will have a higher value than for the normal tissue. Additionally, it is well known that the great majority of carcinomas develop at the sites of epithelial glands. Due to the differences in tissue composition, there is a higher Compton count at the PCa sites relative to non-PCa sites for the same prostate, and also a higher Rayleigh component at PCa sites, although this is much smaller than the Compton intensity.

The XRF measurements of prostatic tissue samples (biopsy cores) are used to measure Zn content by counting fluorescent X-Rays at the Zn characteristic energy, typically at the K-line. The Zn count is then calibrated for possible variations in sample size and thickness by deriving, either from the XRF spectrum, or through a supporting optical imaging system or equivalent means, a calibrated Compton count. Derivation of a calibrated Compton count is well known in the art of XRF analysis.

The inventors of the present disclosure have found that the compounded (Compton+Rayleigh) intensity deduced from the X-Ray spectrum measured from pixels along a prostate core can be used not only to provide a calibration factor regarding the geometry (mass and density) along the sample, but also to establish a correlation with the variations in the epithelial gland density and molecular composition along the sample due to the presence of cancerous or non-cancerous sites in the prostate.

While the parameters used in the present method may be calculated or expressed in various different ways, in one preferred embodiment, the calibrated zinc levels are expressed as Zn, the calibrated relative epithelial tissue measure is expressed as Epi, and the calibrated Zn per volume per amount of epithelial is expressed as Zn/Epi. The mean values and standard deviation ($\sigma$) values of Zn, Epi and Zn/Epi are hereinafter referred to as the XRF Parameters.

FIG. 1 illustrates an exemplified method 100 for generation and normalization of a population database, according to some embodiments of the present invention.

During a biopsy procedure, cores are removed from the prostate and are scanned by XRF. At 102, the XRF Parameters for all the pixels in a core are acquired and sent to a population database 114, and at 104 the XRF parameters for each core are derived and sent to the population database 114. Once all the cores in the biopsy are acquired and scanned, the XRF Parameters for the biopsy are derived 106 from the XRF data for all the pixels from all the cores in the biopsy. Once derived, the XRF biopsy parameters are sent to the population database 114. Additionally, at 108, the core XRF parameters (derived at 104) are normalized relative to the respective XRF parameters of the biopsy they belong to (derived at 106) and the Biopsy Normalized XRF Core parameters are sent to the population database (114*iii*).

Following acquisition of all cores and their XRF scanning, the cores are sent 110 to histo-pathology for classification and grading. The cores are classified by pathology into one of the following categories: (a) Prostate cancer—PCa (Gleason Grade+lesion size). PCa grade classification is based on the Gleason score [Gleason, DF, Hum. Pathol. 23 273-279, 1992; Epstein et al., Am. J. Surg. Pathol. 29 1228-1242, 2005] for a core, which indicates the Gleason grades for the two highest grade and size lesions in a core; (b) Benign—SGH(Stroma and Glandular Hyperplasia) and/or FMH (Fibro Muscular Hyperplasia); and (c) Metabolic—BCH (Basal Cell Hyperplasia); TCM (Transitional Cell Metaplasia); MCI (Mild Chronic Inflammation); AA (Atrophic Accini).

The population database 114 comprises 114*i* the XRF parameters of all cores (from 104) and all biopsies (from 106) as well as 114*ii* the pathology classification for all the cores examined (from 110) and the clinical data for all prostates (112). The population database 114 comprises 114*iv*: the core XRF parameters corresponding to the Pathology Positive cores and their grades, normalized to the XRF Population parameters comprise the Positive Cores XRF Dataset. The population database 114 comprises 114*v* a Positive Biopsies XRF Dataset which comprises the biopsy XRF parameters corresponding to the Pathology Positive prostates and their grades, normalized to the XRF Population parameters.

The XRF Parameters for the Population are derived from the XRF data for all the pixels from all the cores from all the biopsies in the population. Population Data is regularly updated and provides reference XRF Parameters for classification and normalization of each of the cores and biopsies scanned by XRF. The Population Data can be stored in population database 114 locally, as part of the system, or in a cloud storage facility, or both, and can be accessed by the system directly or through the cloud.

Following the analysis of a biopsy and its cores the database of XRF Parameters for the Population of prostates (all pixels all cores all prostates in the population or a subset of the population) is updated.

Experimental Core and Biopsy Classification

Following is a description of measurements performed on 20 patients who underwent TRUS 16 cores biopsy. On average, there were about 10 pixels per core.

Two prostates pathology classified as Prostatitis (Inflammation) showed a very distinct behavior regarding the levels of Zn and Epi and were separately classified. The analysis below does not incorporate the inflamed prostates.

The Inventor found that for a given Prostate, the average amount of Zn for a given Benign core is linearly related to the average Epi level for that core. The proportionality factor varied between individual Prostates. The linear relationship between epithelial cells and Zn was confirmed by comparing visual counts of epithelial cells on pathology slides with Epi values derived from XRF. We found that typically, benign prostates have higher Zn-Epi linear factors and/or a higher Zn baseline.

The Inventor also found that the joint presence of higher Epi levels and lower Zn levels are characteristic of PCa. Therefore a particular Biopsy with such conditions can be assigned with a preliminary PCa classification, and this preliminary PCa classification can be automatically updated during acquisition of additional biopsy data.

Pixel level—a preliminary classification of a core can be performed by comparing simultaneously the behavior of the XRF Parameters for the pixels along a given Core, according to the following exemplified scenarios. (i) The Epi vs. pixel curve for a core has an up or down slope while the Zn vs. pixel curve has a down or up slope respectively for at least two-or more pixels. If the Zn/Epi vs. pixel curve for this core has a low mean value and a medium to high a, this is indicative of a Positive Core. The steepest the slopes (up or down) the highest the PCa grade for the core. (ii) the Epi vs. pixel curve has an up or down slope while the Zn vs. pixel curve is relatively flat and the mean Zn is medium to low—indicative of a Positive Core. (iii) the Epi vs. pixel and Zn vs. pixel curves are relatively flat and the mean Epi is high and the mean Zn is low—Positive and High Grade. The relative size of the lesion (e.g., expressed as percentage of the core) can be determined from the percentage of pixels with positive behavior in the Core. The examples are not exhaustive and statistical approaches to identify the pixels trends (e.g., Pearson Coefficient, a/mean ratios for Zn/epi, and the like) are also contemplated.

The classification of cores according to their Core XRF parameters accounted for the type of prostate the core belonged to, e.g., whether High mean Zn (HiZn) or Low to Medium mean Zn (LoMid Zn) prostate. Low, Medium or High values are relative to the Mean Biopsy Population XRF levels.

It was found that for LOMId Zn prostates: (i) the average Epi of PCa Cores classes are significantly higher than those of the benign classes, (ii) the average Zn of PCa Cores classes are significantly lower than those of the benign classes, and (iii) the mean Zn/Epi for the PCa Cores classes is smaller (and for the majority of the classes, much smaller) than the Benign Cores classes.

For HiZn prostates, the HiZn PCa Cores class had much higher Epi and much lower Zn/epi values than those of the HiZn Benign classes. Without being bound to any particularly theory, it was observed that (i) Carcinomas develop dominantly (95% of cases) in epithelial sites; (ii) Zn predominantly accumulates in the epithelial cells in the prostate; and (iii) Zn depletes from the epithelial cells in cancerous prostate sites.

Accordingly, it was concluded that Pixels/Cores with higher Epi and smaller Zn are indicative of PCa, and Cores with very high Zn and/or high ratio Zn/epi (characteristic of low or no Zn depletion) are typically Negative.

Figure 2:
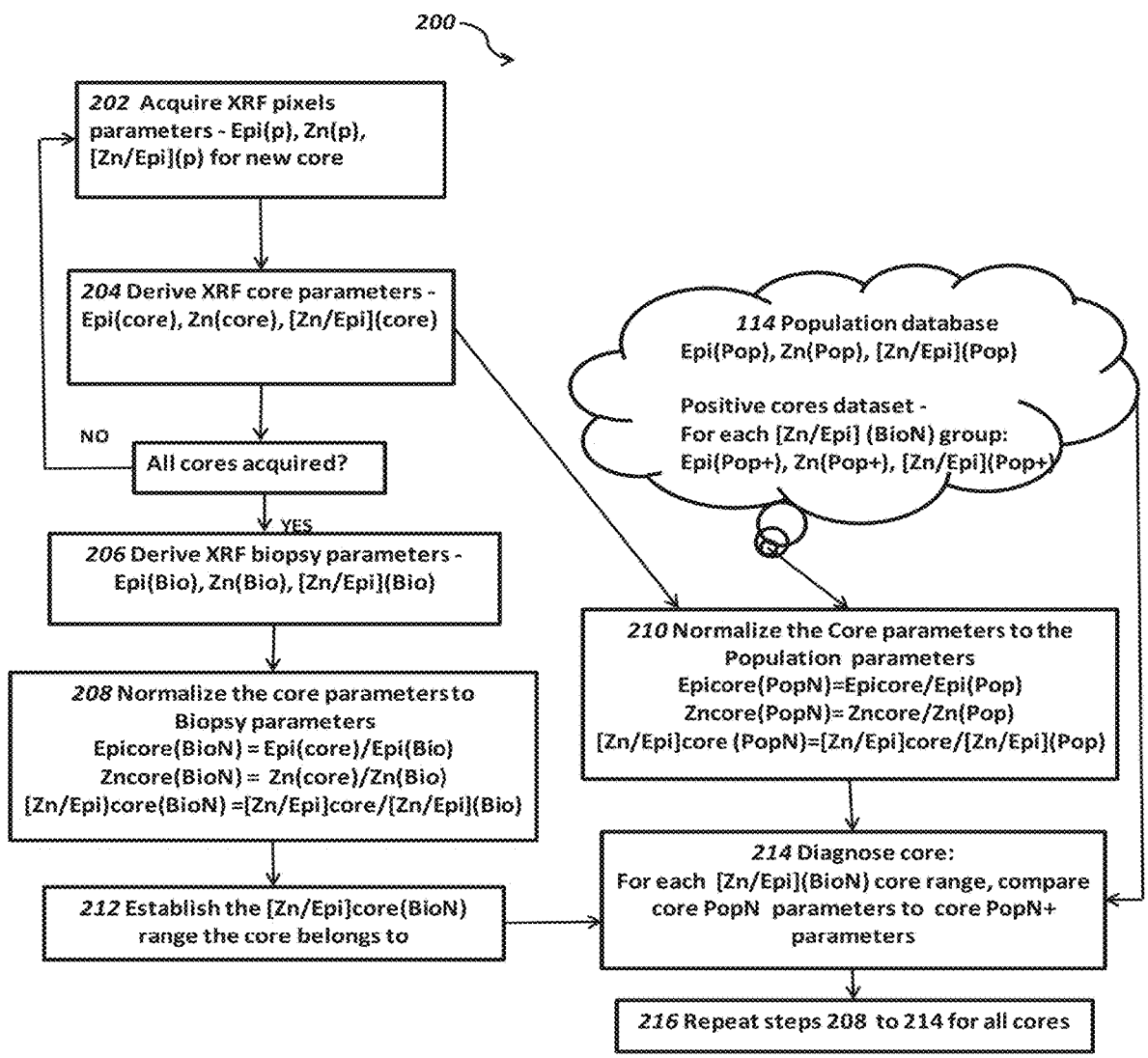
FIG. 2 is a flowchart of a method of core diagnosis according to embodiments of the present disclosure.

FIG. 2 illustrates a method 200 of core classification/diagnosis. The operations described in FIG. 2 are optionally and preferably performed for each Core and for each Biopsy. XRF parameters are acquired 202 for all the Pixels in the Core. The XRF Parameters for the Core (all Pixels) are derived 204. Operations 202 and 204 are repeated for each new core until all cores are acquired. Once all cores are acquired, the XRF Parameters for the Biopsy (all pixels all cores) are derived 206. At 208, the XRF Parameters of each and all cores in the biopsy are normalized to the Biopsy XRF Parameters (BioN). The following notations are used normalization 208: Epicore (BioN)=epi (core)/epi(Bio), Zncore (BioN)=Zn(core)/Zn(Bio), and (Zn/Epi)core (BioN)=(Zn/epi) (core)/(Zn/epi)(Bio). At 210 the XRF Parameters of each and all cores in the biopsy are normalized to the Population (Pop) XRF Parameters (PopN). The following notations are used for normalization 210: Epicore (PopN) =epi(core)/epi(Pop), Zncore (PopN)=Zn(core)/Zn(Pop), and (Zn/Epi)core(PopN)=(Zn/epi) (core)/(Zn/epi)(Pop).

In some embodiments, the diagnostic classification at the individual level of cores from different biopsies is based on comparing between cores that have (Zn/Epi)(core)(BioN) values within a common range, e.g., do not differ by more than 5-10%, as if they belonged to the same biopsy.

At 212 a (Zn/Epi)(core)(BioN) range the core belongs to is established. A core diagnosis is performed 214 by comparing between the Population Normalized XRF parameters of the given core and the Population Normalized XRF parameters (PopN+) of cores from the Positive cores dataset within the same (Zn/Epi)(core)(BioN) common range from 212. Operations 208 to 214 are repeated 216 for all the cores in the particular Biopsy.

Figure 3:
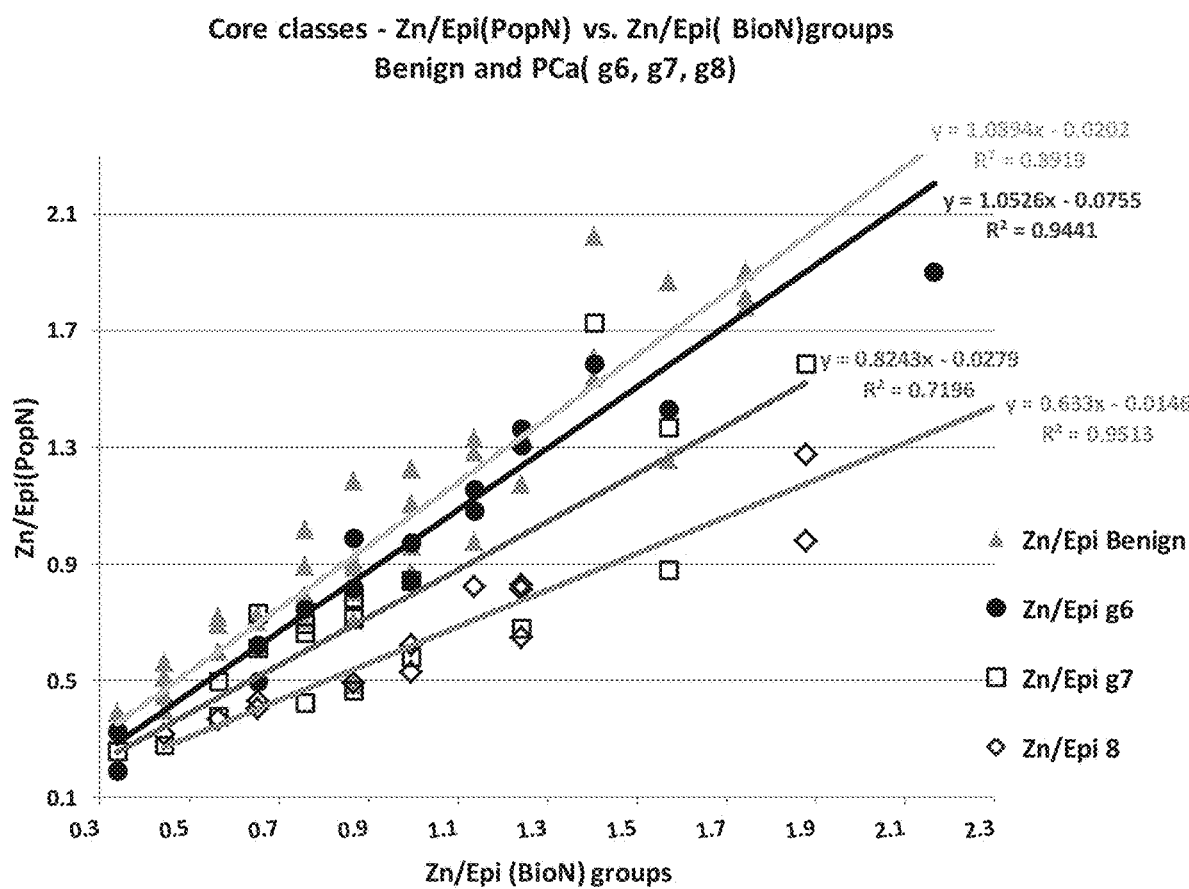
FIG. 3 is a graph illustrating differentiation of core classes according to embodiments of the present disclosure.

FIG. 3 shows the relationship between the values of (Zn/Epi)core(PopN) as a function of (Zn/Epi)(core)(BioN) range for 4 types of cores found in the present study: (i) Benign, (ii) PCa g6, (iii) PCa g7, and (iv) PCa g8. As shown there is a differentiation between values of (Zn/Epi)core (PopN) for the higher PCa grades (g7 and g8) and the Benign cores. The differentiation between PCa grade g6 and benign is less pronounced, but when cores from a same prostate are compared the differentiation is sharper.

It was further found on a global level that the majority of the pathology P cores had higher Epicore(PopN) and/or lower (Zn/epi)core(PopN) or Zn(core)(PopN) than the pathology N cores. For PCa cores, epi(core)PopN which is larger than or equal to 1.2 and/or Zn(core)PopN which is lower than or equal to 0.8 are strong indicators of high grade. Additionally, 25% of the cores pathology classified as benign (N) had values of Zn(core)PopN or (Zn/epi(core) PopN higher than established upper Negative threshold values. These XRF parameters correspond to cores where there was little or no Zn depletion indicative of PCa. Out of these a single core was FN (corresponding to a sensitivity >95%).

Figure 4:
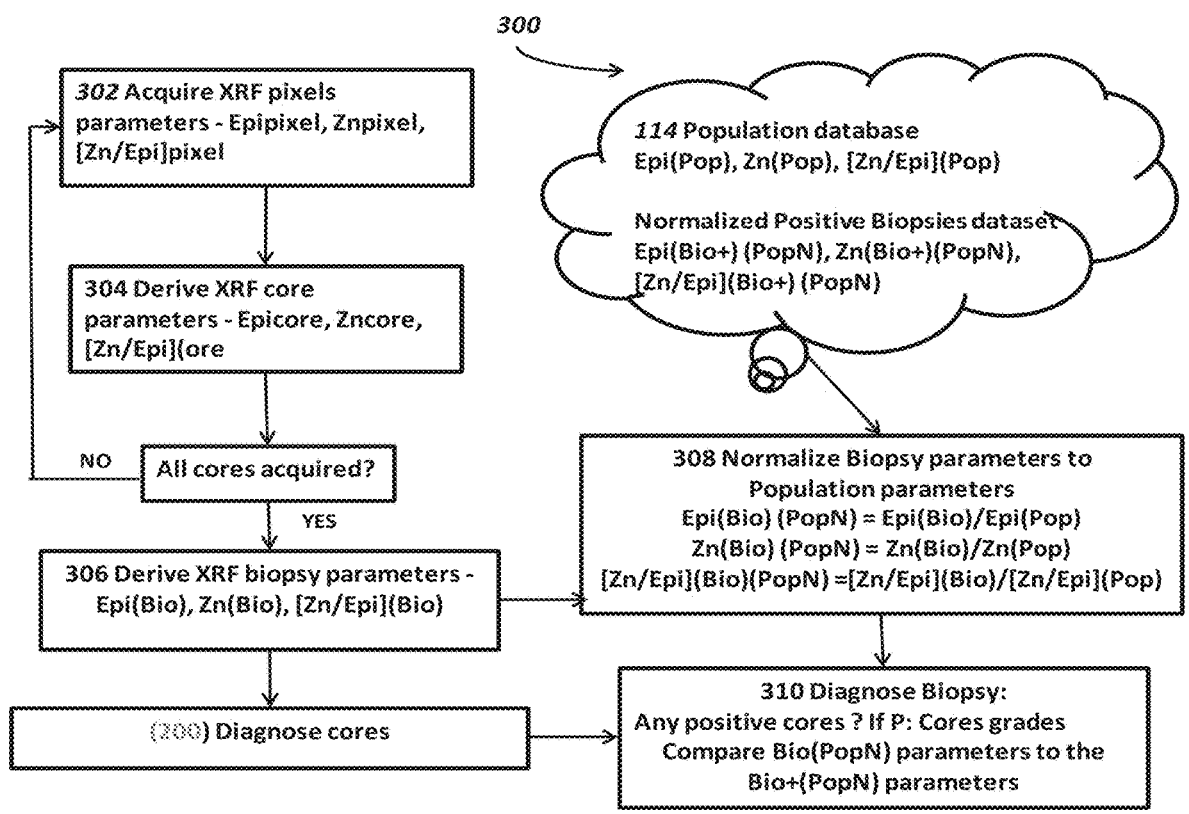
FIG. 4 is a flowchart of a method of biopsy diagnosis according to embodiments of the present disclosure.

FIG. 4 is a flowchart of a method 300 of biopsy diagnosis according to embodiments of the present disclosure. The biopsy XRF parameters and the clinical parameters of the biopsy patient, e.g., PSA and Prostate Volume, provide a preliminary classification of the biopsy type as PCa (P) or Benign (N), simultaneously and complementary to the analysis at the core level for the particular prostate under examination. The correlation between volume and PCa for the data acquired was weak. Out of the 18 prostates analyzed, there were 11 biopsies with PSA <10 ng/ml—6N and 5P—and 7 biopsies with PSA>10 ng/ml—2N and 5P. The average values of Epi(Bio) for the positive biopsies were found to be higher than for the negative biopsies and in particular for the two low ranges: PSA<6 ng/ml and 6 ng/ml<PSA<10 ng/ml. The following biopsy (prostate)

diagnosis procedure was used. For each Core and for each Biopsy: the XRF parameters for all the Pixels in the Core were acquired 302. The XRF Parameters for the Core were derived 304. Operations 302 and 304 were repeated for all cores in the biopsy. Once all cores were acquired, the XRF Parameters for the Biopsy (all pixels all cores) was derived 306. The XRF Biopsy Parameters were normalized 308 to the Population (Pop) XRF Parameters. The following notation were used for the normalization 308: EpiBio(PopN) =epi(biopsy)/epi(Pop), ZnBio(PopN)=Zn(biopsy)/Zn(Pop), and (Zn/Epi)Bio(PopN)=(Zn/epi) (biopsy)/(Zn/epi)(PopN).

At 200 the cores were diagnosed. The diagnostic classification 310 of biopsies was based on the number and grades of Positive cores found in 200, if any, and by comparing between the Population Normalized XRF parameters of the given biopsy (from 308) to the Population Normalized XRF parameters of pathology positive biopsies from the Positive biopsies dataset in the population database 114.

A statistically significant differentiation between the XRF parameters for Pathology classified Negative Prostates and the XRF parameters for Pathology classified Positive prostates (biopsies) was found, as follows. Prostates with very low mean Epi are typically benign, Prostates with very high mean Epi are typically PCa Prostates with very high mean Zn/Epi are typically benign, and Prostates with mid to mid-high levels of Epi and low levels of Zn are typically PCa high grade prostates having a large number of PCa cores.

Figure 5:
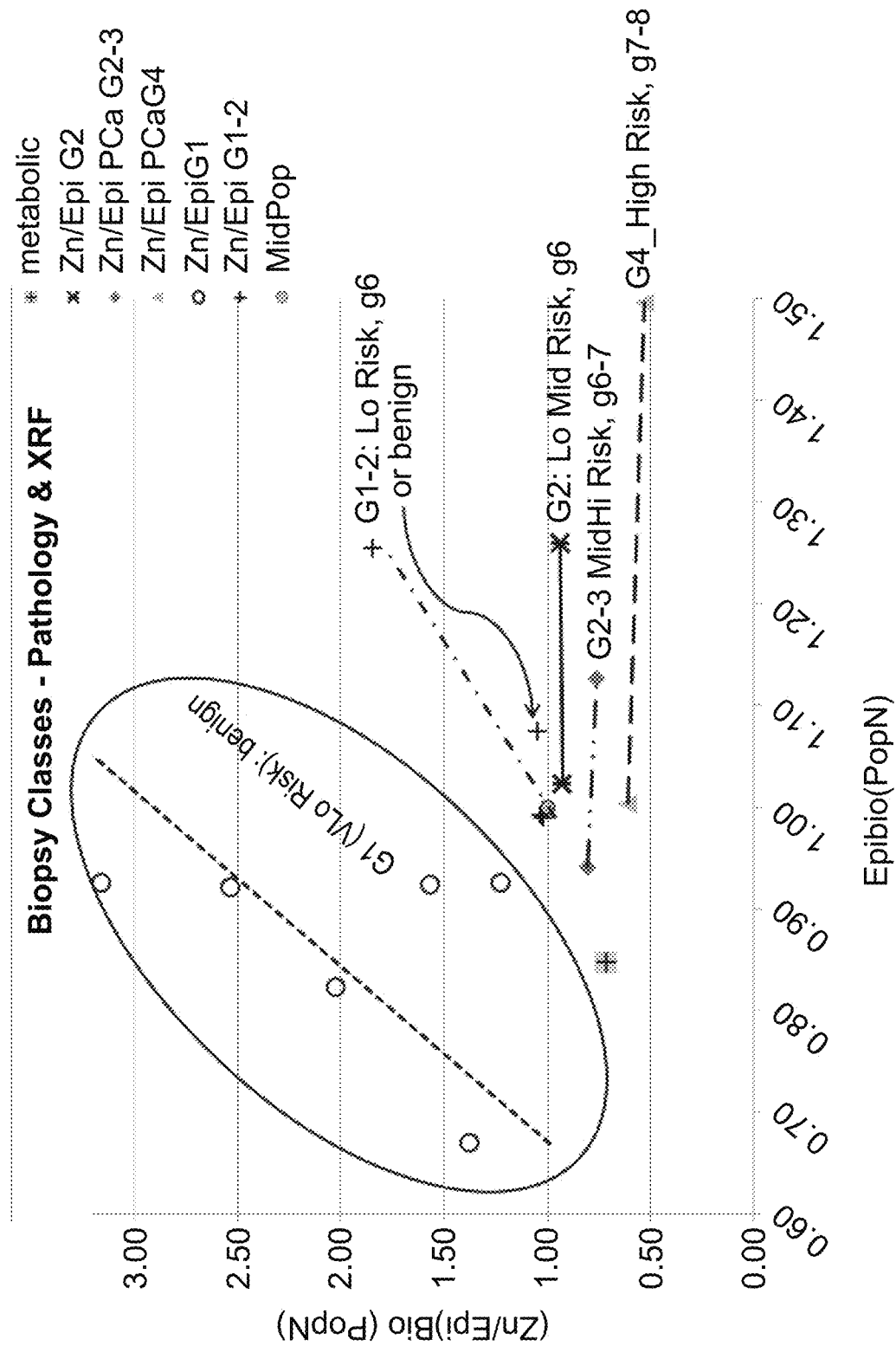
FIG. 5 is a graph illustrating differentiation of biopsy classes according to embodiments of the present disclosure.

FIG. 5 is a graph illustrating differentiation of biopsy classes. Biopsies were grouped according to their pathology classification: PCa (P) or Benign (N). Positive Biopsies were classified according to the higher grades of the P cores identified by pathology. The prostate grade scores used in the current clinical practice range from G1 (<=g6) to G5 (g9/g10). The classes of the biopsies examined were: G1(g6); G2/3(g6/g7); and G3/4 (g7/g8). No biopsies with higher core grades (g9 or g10) were found in the example study.

It was found that the majority (8 out of 10) of the pathology positive (PCa) prostates had mean EpiBio(PopN) above 0.99. All prostates (4 out of 4) with mean EpiBio (PopN) above 1.12 were positive. All prostates (6 out of 6) with mean (Zn/Epi)Bio(PopN) less than 0.95 and EpiBio (PopN) above 0.94 were Positive. Correctly accounted for 9 out of 10 Positive Biopsies (9TP). The majority (6 out of 8) of the pathology benign prostates had mean EpiBio(PopN) less than 0.94 and/or mean (Zn/Epi)Bio(PopN) above 1.2. Correctly accounted for 7 out of 8 Negative Biopsies (7 TN). All (4 out of 4) prostates with the highest grades (G3-G4) had mean (Zn/Epi)Bio(PopN) less than 0.8.

The cores diagnosis 200 and biopsy diagnostic 300 above were tested on a dataset obtained from about 300 cores extracted from 20 patients. The results are provided in Table 1.

TABLE 1

Cores diagnosis statistics

| | Total Cores | P | N | TP | TN | FP | FN |
|---|---|---|---|---|---|---|---|
| All cores all biopsies | 297 | 68 | 229 | 60 | 222 | 7 | 8 |

This Example is additionally directed at establishing the presence of cancer and its level of malignancy ("Cancer Risk Assessment") in a bodily organ, based on measuring physical and biological characteristics of the organ tissue at several locations in the organ, at a minimum number of sites, typically 4-6 local sites, and deriving from these measurements the levels of at least two cancer biomarkers for the organ, both for each location measured as well as for the whole organ. In particular, this Example is targeted at detecting and establishing the Risk Level of Cancer in a Prostate.

Figure 6:
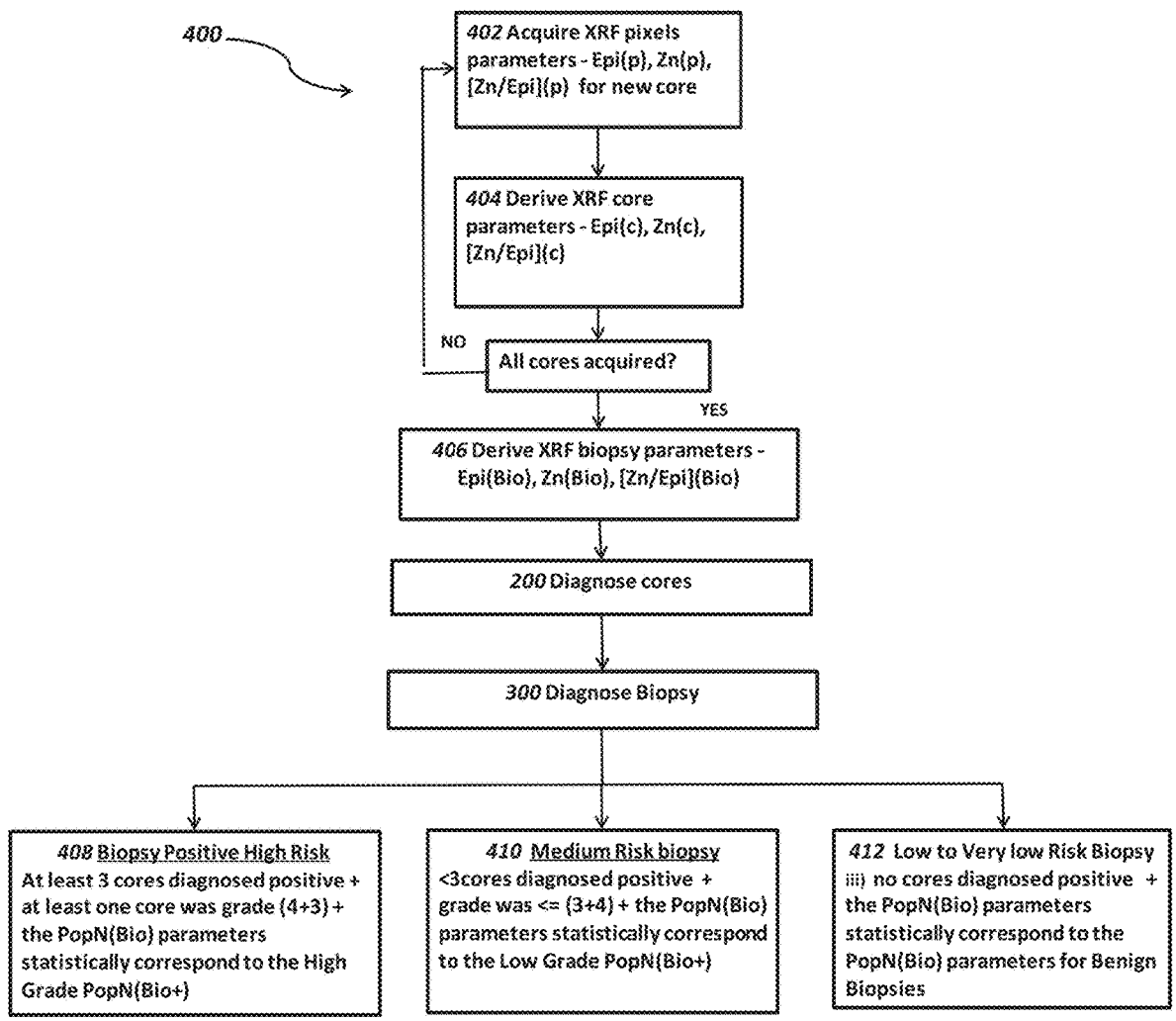
FIG. 6 is a flowchart of a method of risk assessment according to embodiments of the present disclosure.

FIG. 6 is a flowchart of a method 600 of risk assessment according to embodiments of the present disclosure in which the organ is a prostate and the biomarkers are Zn and Epi. Tissue samples (biopsy cores) are acquired in the context of a prostate biopsy. Each core is scanned by XRF at a predetermined scanning resolution, providing 402 the levels of Zn, Epi and Zn/Epi for several scanned pixels in each core. At 404, the XRF parameters for each core removed and scanned are derived and once all cores are acquired, the XRF parameters for the Biopsy are derived 406. Subsequently, each core is diagnosed (e.g., by following selected operations of method 200), the Biopsy is diagnosed (e.g., by following selected operations of method 300) and the Risk of the prostate is established 408-412. In some embodiments, the presence and malignancy grade of a cancer at one or more local sites in the prostate (PCa—Local cancer grade) is characterized by higher levels of epithelial and lower levels of Zn (herein referred to together as "Zn depletion"), and the greater the Zn depletion, the higher the grade of the cancer in the site.

Additionally, the Zn and Epithelial Biomarker Information for the individual prostate ("Biopsy"), is used to establish the cancerous risk level, or benign or pre-cancerous risk level. The cancer grade for the individual prostate is established using the Biopsy XRF parameters and relationships between them that are indicative of local Zn depletion.

Additionally the number, location and grade of the positive cores found, if any, are also considered in when establishing the risk assessment for the patient under examination.

Accordingly, the risk assessment (for example, level of cancer malignancy in the prostate) is established. This is optionally and preferably done using the following set of criteria. High risk 408 corresponds to high grade cancer found in the majority of the measured local sites in the prostate and the prostate grade is high. Medium risk levels 410 correspond to intermediate conditions where low to medium grade cancers are found at only a single or few of the measured local sites in the prostate and the prostate grade is positive but low grade. Low risk 412 corresponds to no cancers found at any of the measured local sites in the prostate and the prostate grade is negative. The final positivity grade or level of a given prostate and the related Patient Cancer Risk Assessment are derived from the actual number of positive cores found during the biopsy out of all the cores measured (CDR), the grades of all the positive cores found and the Prostate Positivity Grade.

This Example also provides a technique that allows the reduction of the number of cores removed during a prostate biopsy while simultaneously substantially improving the sensitivity of the procedure. This can substantially reduce the number of False Diagnostic results.

A core removal scheme according to some embodiments of the present invention can lead to higher Cancer Detection Rates (CDR) while removing less cores than the current standard (12 cores or more in TRUS biopsies). In a study performed by the Inventor, sixteen (16) cores were removed from each prostate during the biopsy according to a removal scheme 500 illustrated in FIG. 7. Eight cores were removed from each side of the prostate. The cores were removed from the Base (the upper region of the prostate close to the urethra), the Apex (the lower region of the prostate), and the region between them (Mid Gland), starting from the far lateral left (LL), then mid lateral left, then far lateral right (RL) and mid lateral right.

The overall incidence of positive cores in the low grade prostates (G1-G2) was less that 20%, with the exception of one prostate with 9 Positive (P) Gleason grade 6(3+3) cores. For these prostates, the incidence of P cores was higher in the Mid Gland and Apex regions and much smaller in the Base region (only 2P out of 27 cores in the region). The overall incidence of P cores per biopsy for the 3 high grade (G3-G4) prostates was about 90%.

Figure 7:
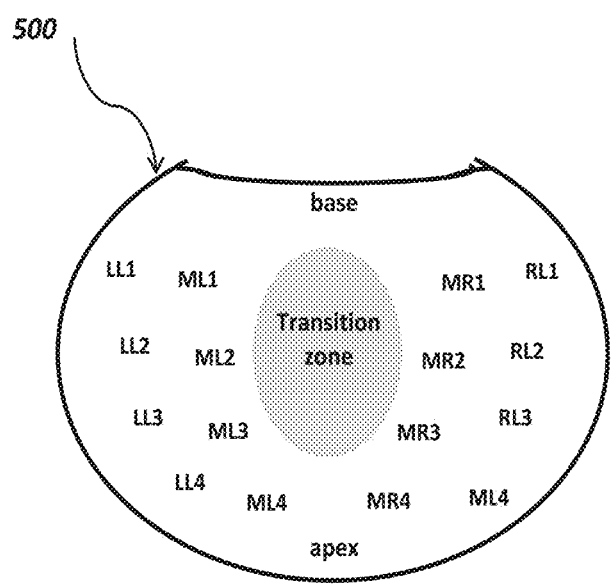
FIG. 7 is a schematic diagram showing a scheme of core removal from a prostate.

Accordingly a higher overall detection rate of P cores can be achieved according to an initial removal scheme where 6 cores are removed, three (3) cores from each side of the prostate, from sites in the upper mid-gland-line LL2-RL2; lower mid-gland-line LL3-RL3 and the Apex adjacent line LL4-RL4 as shown in FIG. 7. Initially, no cores are removed from the upper Base adjacent line.

It was surprisingly found that the incidence of Positive cores in a prostate is not symmetrical. One side can have positive cores while the opposite side has only benign cores.

In a study performed by the Inventor, the six-cores scheme of the present embodiments successfully identified 16 out of 23 P cores from the six Positive low grade (G1) prostates and one grade G2 prostate examined in the study. For all the low grade biopsies, at least one of the P cores have been identified.

Figure 8:
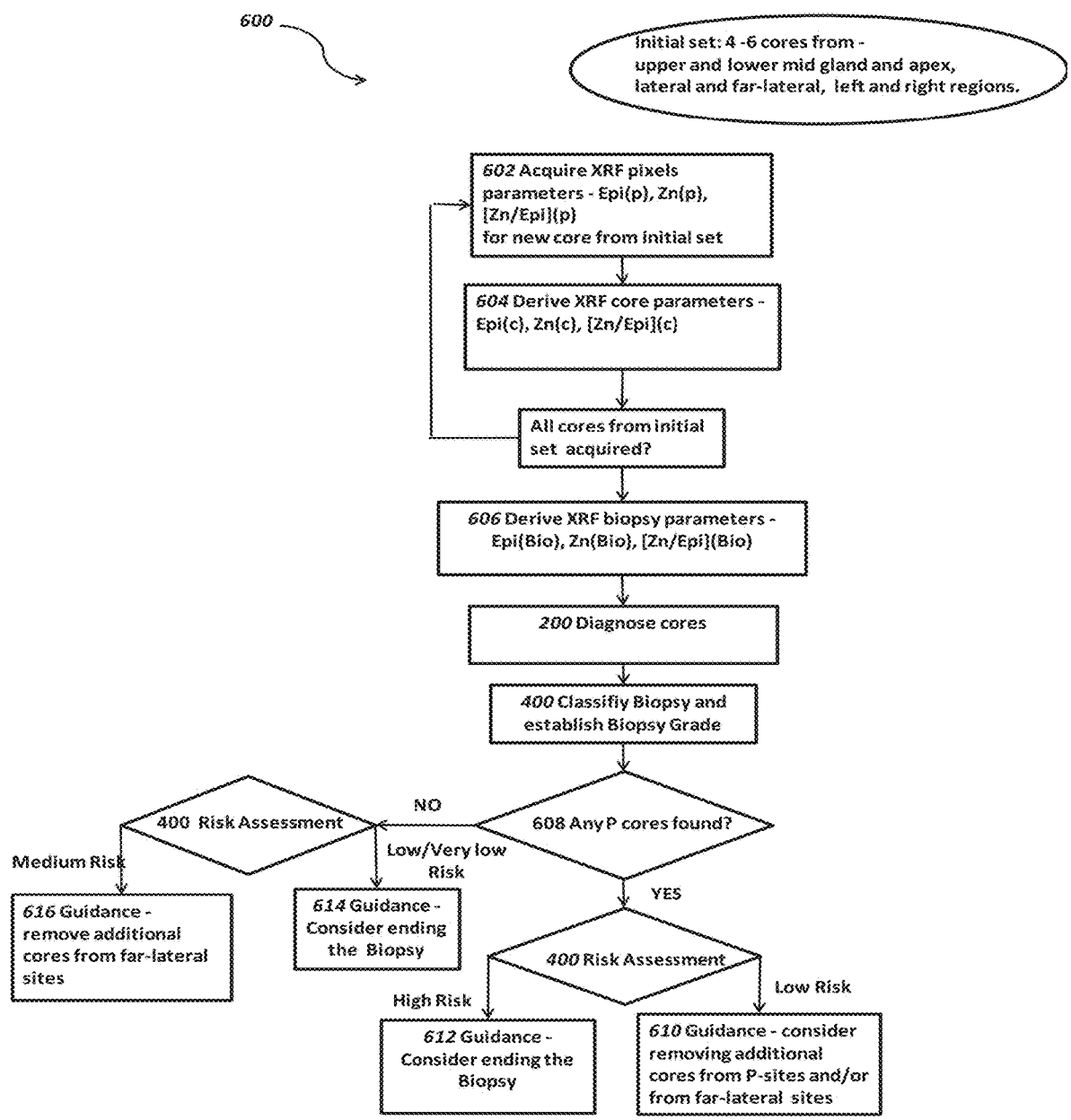
FIG. 8 is a flowchart of a method of biopsy guidance according to embodiments of the present disclosure.

FIG. 8 is a flowchart of a method 600 of biopsy guidance according to embodiments of the present disclosure. XRF pixel parameters are acquired 602 for an initial set of at least 4 but not more than 8 cores, e.g., about 6 cores, from the prostate according to a lateral mid gland and apex initial scheme: upper and lower mid gland and apex, lateral and far-lateral, left and right regions, and Core XRF Parameters are derived 604. Once all cores from the initial set are acquired, the Biopsy XRF Parameters are derived 606. The cores can be diagnosed (e.g., by executing selected operations of method 200) and the Biopsy can be classified, and optionally also graded (e.g., by executing selected operations of method 300). If the prostate is positive, at least one P core is identified.

When one or more P cores are identified 608, the grade of the core is established and guidance is provided according to the Risk Assessment of the prostate. When the number of identified P cores is low (e.g., about 20%), the method recommends 610 extracting more cores from sites close to the identified positive sites and/or from additional sites in the aforementioned regions. In case positive cores would be found only in one side of the prostate, the method can recommend that further cores would only be removed from that side.

When the number of identified P cores is high (e.g., more than 60%), the method can recommend 612 to stop the biopsy since the prostate risk prognosis is already complete.

When no P cores are found in either side of the prostate, it is highly probable that the prostate is benign and that the probability of finding a P core through removal of further cores is very low. Additionally, if a P core would be found through removal of further cores, the probability that this P core would be of low grade (g6) is high. In this case, if the derived Biopsy positivity is very low or low, the method preferably recommends 614 ending the Biopsy. On the other hand, if the derived Biopsy positivity is low or medium, the method can recommend 616 extracting more cores from additional sites in the prostate to further decrease the possibility of a False Negative. For the case of large volume prostates, typically above 80 cc, it is preferred to remove further cores in the region between the sites of the scheme described.

Figure 9:
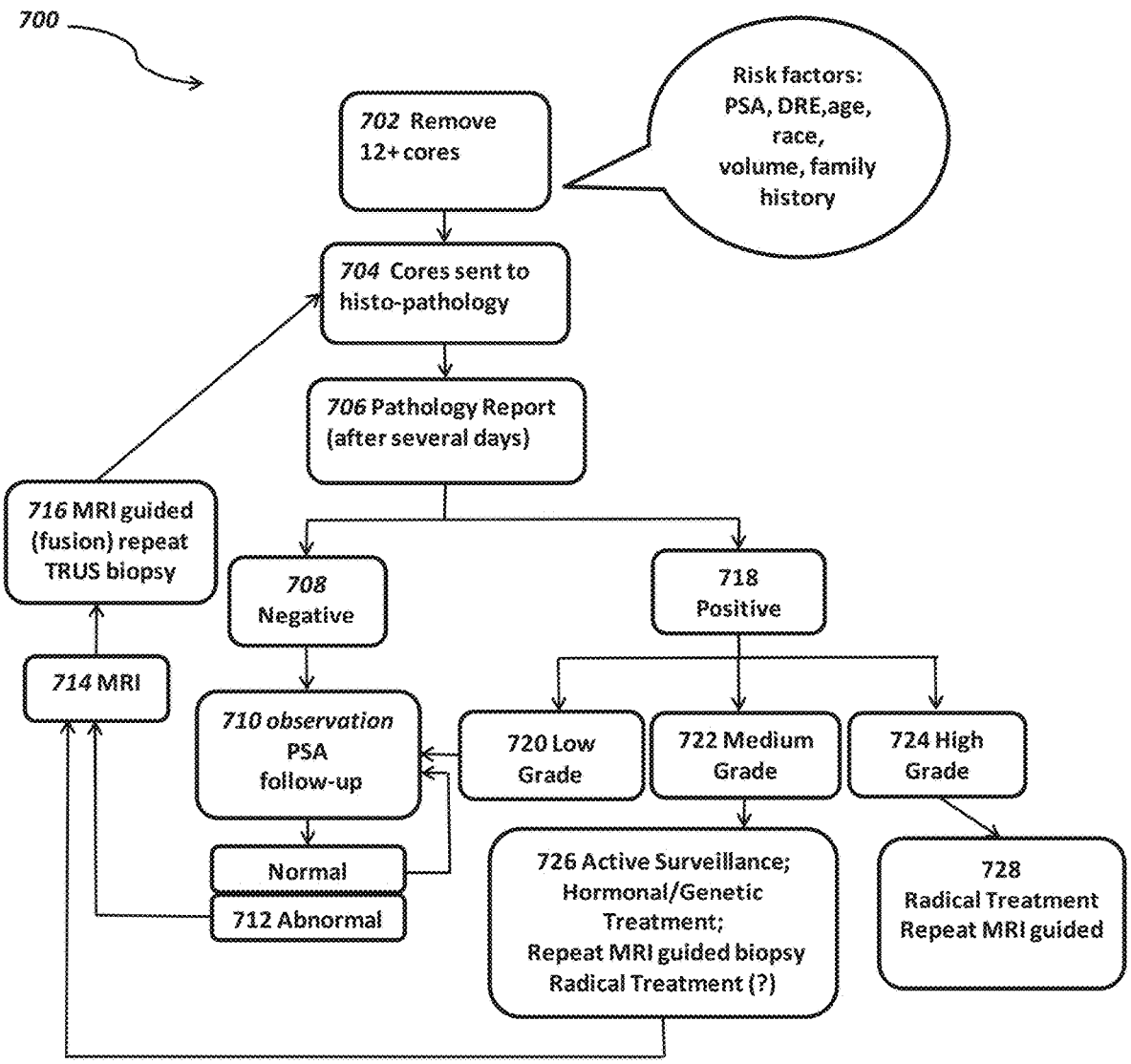
FIG. 9 is a flowchart of a representative biopsy of a prostate, such as TRUS biopsy or TP biopsy.

FIG. 9 is a flowchart of a representative TRUS or TP biopsy procedure 700, with post biopsy pathology diagnosis and external (typically Genomic based) Risk Assessment. In this procedure, a large number of biopsy samples (12 cores and more) are removed 702 in a random, unguided biopsy procedure. The samples are then sent to histo-pathology 704 for diagnosis that is provided only several days after the procedure 706. No biomarker information is gathered or provided neither during the biopsy procedure nor during the pathology. Pathology provides the grades and lesion sizes of the positive cores found and where relevant indicate other metabolic processes present. If the pathology report is negative 708 the patient follow-up typically includes clinical observation and one or more PSA based tests 710 and if abnormal 712, the patient is typically sent to MRI imaging 714 followed by MRI guided fusion TRUS repeat biopsy 716, and all the steps up to the pathology report are repeated one or more times until either a positive diagnosis is reached or a decision is taken to perform a saturated biopsy, where a much larger amount of cores are removed from the prostate. If the pathology report is positive, 718, the operations differ according to the prostate pathology grade (Low, Medium and High grade levels) according to the highest core grade found and the overall number of positive cores found during the biopsy. For the Low Grade case 720, the typical treatment route is similar to the Negative pathology case 708 and comprise of observation 710 that includes clinical and PSA follow-up and if necessary 712 a repeat MRI guided TRUS biopsy 714-716 before active surveillance and drug treatment. The main difference is in the time frame for PSA follow-up. For the Medium Grade case, the typical treatment route comprises Active Surveillance 726 that includes, more frequent PSA and/or other tests followup (Hormonal/Genomic) and MRI guided repeat biopsy before a more radical treatment like radiation therapy and/or Radical Prostatectomy. For the High Grade case, the typical treatment route 728 is Radical Treatment, possibly preceded by MRI guided saturated biopsy for staging.

The Cancer Detection Rate (CDR) and Positive Yield of the TRUS procedure described above with respect to FIG. 9 are low, the False Negative is high and the actual Cancer Risk Assessment is poor and except for High Grade prostates, for which Radical Treatment is usually recommended, the treatment options and decision are limited and would typically require additional expensive (Genomic) tests and/ or MRI fusion guided biopsy procedures for Risk Assessment and treatment determination.

Figure 10:
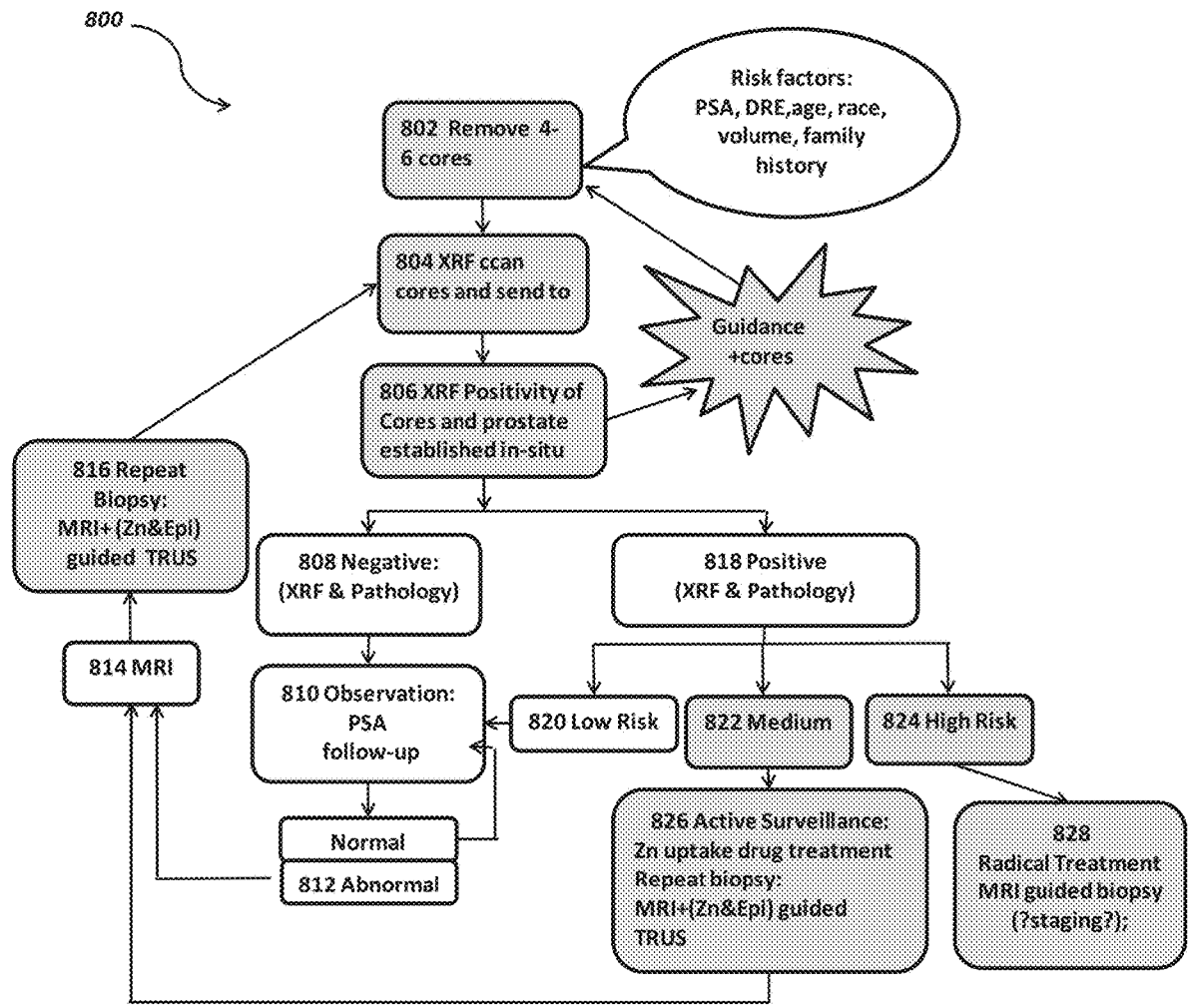
FIG. 10 is a flowchart of a method of Zn and epithelial based trans-rectal ultrasound biopsy according to embodiments of the present disclosure.

FIG. 10 is a flowchart of a method 800 of Zn and epithelial based trans-rectal ultrasound biopsy according to embodiments of the present disclosure. Method 800 optionally and preferably includes a Zn and Epithelial based biopsy procedure, which include fast (e.g., within less than an hour, or less than 50 minutes, or less than 40 minutes, or less than 30 minutes, or less than 20 minutes, or less than 10 minutes) diagnosis feedback during the biopsy ("Interactive Biopsy") and the Risk Assessment derived through the use of the dual Zn and Epithelial biomarkers in the proposed method.

Following the removal 802 of an initial number of biopsy cores, typically 4-6 cores, and their scanning 804 by XRF the positivity and grade of each of the cores and of the prostate itself are established 806 based on the XRF parameters for each core and collectively, for the prostate (biopsy) itself ("Biomarker Positivity"). The positivity of the prostate optionally and preferably takes into account the number of positive cores found and the grades of each positive core found.

The in-situ analysis of the cores and the prostate is used to provide feedback and guidance to the practitioner to either end the procedure if no positive cores are found and the biomarkers positivity of the prostate is low; or, conversely, if positive cores are found and the biomarkers positivity of the prostate is high, the method provides guidance to the practitioner during the biopsy itself indicating sites of higher cancer probability from where further cores can be removed.

For the case of an in-situ Negative Prostate Positivity diagnosis 808 (e.g., no positive cores found), the operations following the end of the cores removal 810-814 are similar to those described above with respect to FIG. 9. At 816 MRI guided biopsy is repeated in order to confirm/the presence of PCa at or around MRI identified lesions.

For the case of Positive Prostate diagnosis 818, the operations differ according to the Risk level for the prostate (Low, Medium and High Risk levels as defined in FIG. 6, see 408, 410, and 412, respectively). For the Low Risk case, the typical treatment route can be similar to the Negative pathology case and comprise of operations 810 to 816 that include clinical and PSA follow-up, and, if necessary, an MRI guided biopsy incorporating the Zn and Epi biopsy method of the present embodiments, before active surveillance and drug treatment. The main difference would be in the time frame for PSA follow-up.

For the Medium Risk case 822, the typical treatment route can comprise Active Surveillance 826 that would include more frequent PSA and/or other screening tests follow-up and, when necessary, an MRI guided biopsy 816 incorporating the Zn and Epi based method of the present embodiments, before a more radical treatment such as radiation therapy and/or Radical Prostatectomy.

For the High Risk case 824, the typical treatment route can be Radical Treatment 828, possibly preceded by MRI guided saturated biopsy for staging.

The accurate Risk Assessment in accordance with some embodiments of the present invention, provides adequate treatment for the patient. The capability of the technique of the present embodiments to distinguish accurately and firmly between the three cases is achieved by applying selected operations of method 500 (FIG. 6). A particular advantage of the technique of the present embodiments is that there is no need to perform expensive Genomic tests in order to establish the Risk Assessment and Prognosis following the biopsy.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A biopsy method, the biopsy method comprising:
   extracting from a prostate gland of a subject, by a core biopsy needle, a biopsy sample containing tissue;
   measuring X-Ray Fluorescence (XRF) spectrum from the sample and extracting from said spectrum zinc level and an epithelial glandular tissue concentration in the sample, wherein said extracting said epithelial glandular tissue concentration comprises differentiating between contributions of an inelastic scattering component and an elastic scattering component to said spectrum, and estimating said epithelial glandular tissue concentration based, at least in part, on said elastic scattering component contribution;
   based on at least said zinc level and said epithelial glandular tissue concentration in the sample, selecting locations within said prostate gland from which additional biopsy samples are to be extracted; and
   extracting from said locations within said prostate gland, by said core biopsy needle, additional biopsy samples.

2. The method according to claim 1, comprising calculating a ratio between said zinc level and said epithelial glandular tissue concentration, and determining a likelihood that the sample is cancerous based, at least in part, on said calculated ratio.

3. The method according to claim 1, comprising determining a likelihood that the sample is cancerous by thresholding.

4. The method according to claim 1, being executed for a plurality of biopsy samples of the same prostate gland, and comprising normalizing zinc level and epithelial glandular tissue concentration in each individual sample, respectively by a combined zinc level and a combined epithelial glandular tissue concentration.

5. The method according to claim 2, being executed for a plurality of biopsy samples of the same prostate gland, and comprising normalizing in each individual sample, zinc level, epithelial glandular tissue concentration, and said ratio between said zinc level and said epithelial glandular tissue concentration, respectively by a combined zinc level, combined epithelial glandular tissue concentration, and a combined ratio between said zinc level and said epithelial glandular tissue concentration.

6. The method according to claim 4, comprising using said zinc level and said epithelial glandular tissue concentration in said sample to calculate at least one biopsy parameter characterizing said prostate gland.

7. The method according to claim 6, comprising normalizing each of said at least one least one biopsy parameter by a respective biopsy population parameter characterizing a population of prostate glands.

8. The method according to claim 6, comprising normalizing each of said at least one biopsy parameter by a respective biopsy population parameter characterizing a population of cancerous prostate glands, and normalizing each of said at least one biopsy parameter by a respective biopsy population parameter characterizing a population of benign prostate glands.

9. The method according to claim 6, comprising:
   accessing a computer-readable medium storing a library having a plurality of entries, each comprising annotation information of a particular population, and at least one biopsy population parameter characterizing said particular population;

searching said library for an entry having a biopsy population parameter that best matches said biopsy parameter; and extracting annotation information from said found entry.

10. The method according to claim 6, comprising:

accessing a computer-readable medium storing a library having a plurality of entries, each comprising annotation information of a particular population, and at least one biopsy population parameter characterizing said particular population;

determining similarity between said biopsy parameter and biopsy population parameters of at least two entries;

extracting annotation information from said at least two entries; and generating an output pertaining to said similarities and said extracted annotation information.

11. The method according to claim 9, wherein annotation information of at least one entry comprises indication that a respective population is cancerous, and wherein annotation information of at least one entry comprises indication that a respective population is benign.

12. The method according to claim 9, wherein annotation information of at least one entry comprises indication that a respective population is cancerous and indication pertaining to a cancer grade of said respective population.

13. The method according to claim 1, comprising determining a likelihood that the sample is cancerous for each biopsy sample, thereby providing a plurality of likelihood values, and determining a cancer grade of said plurality of biopsy samples, based on said plurality of likelihood values.

14. The method according to claim 1, being initially executed for no more than eight of biopsy samples of the same prostate gland.

15. The method according to claim 1, being executed before the biopsy sample undergoes any treatment or physical or chemical processing.

16. A system for analyzing a biopsy sample containing tissue extracted from a prostate gland of a subject, the system comprising:

a robotic arm configured for extracting biopsy samples from the prostate gland of the subject;

an X-Ray Fluorescence (XRF) system configured for obtaining XRF data from the sample; and a data processor, configured to receive said XRF data, to extracting from said data zinc level, to extract from said data an epithelial glandular tissue concentration based on contribution of an elastic scattering component to said data, to determine a likelihood that the sample is cancerous based on at least said zinc level and said epithelial glandular tissue concentration in the sample, and to instruct said robotic arm to extract an additional biopsy sample, based on said likelihood.

* * * * *